US009028810B2

(12) United States Patent
Lee et al.

(10) Patent No.: US 9,028,810 B2
(45) Date of Patent: May 12, 2015

(54) COMPOSITION FOR INDUCING MIGRATION OF NEURAL STEM CELLS CONTAINING PERIOSTIN AS EFFECTIVE INGREDIENT

(75) Inventors: Myung Ae Lee, Seoul (KR); Jeong Yong Jeon, Gyeonggi-do (KR)

(73) Assignee: Ajou University Industry—Academic Cooperations Foundatin, Gyeonggi-Do (KR)

( * ) Notice: Subject to any disclaimer, the term of this patent is extended or adjusted under 35 U.S.C. 154(b) by 358 days.

(21) Appl. No.: 13/165,322

(22) Filed: Jun. 21, 2011

(65) Prior Publication Data

US 2012/0156175 A1 Jun. 21, 2012

(30) Foreign Application Priority Data

Dec. 20, 2010 (KR) ........................ 10-2010-0130889

(51) Int. Cl.
*A61P 35/00* (2006.01)
*A61K 35/12* (2006.01)
*A61P 25/00* (2006.01)
*C12N 5/0797* (2010.01)
*A61K 38/17* (2006.01)
*A61P 25/28* (2006.01)
*C07K 14/47* (2006.01)
*C12N 5/0793* (2010.01)

(52) U.S. Cl.
CPC .............. *C07K 14/47* (2013.01); *C12N 5/0619* (2013.01); *C12N 5/0623* (2013.01); *C12N 2501/998* (2013.01); *A61K 38/1709* (2013.01)

(58) Field of Classification Search
None
See application file for complete search history.

(56) References Cited

FOREIGN PATENT DOCUMENTS

| KR | 10-2004-0013997 A | 2/2004 |
| KR | 10-2006-0093269 A | 8/2006 |
| KR | 10-2007-0036289 A | 4/2007 |
| WO | WO/2005/062055 A2 | 7/2005 |

OTHER PUBLICATIONS

Kim, Seung-Ki; et al; "Human Neural Stem CellsTarget Experimental Intracranial Medulloblastoma" Clinical Cancer Research, 12, 5550-5556, 2006.*
Yoshioka, Naohisa; et al; "Suppression of Anchorage-Independent Growth of Human Cancer Cell Lines by the TRIF52/Periostin/OSF-2 Gene" Experimental Cell Research, 279, 91-99, 2002.*
Li, Shaoyi; et al; "Potent Bystander Effect in Suicide Gene Therapy Using Neural Stem Cells" Oncology, 503-508, 2005.*
Li, Shaoyi; et al; "Bystander effect-mediated gene therapy of gliomas using genetically engineered neural stem cells" Cancer Gene Therapy, 12,600-607, 2005.*

K. S. Aboody et al., "Neural stem cells display extensive tropism for pathology in adult brain: Evidence from intracranial gliomas", PNAS, 2000, pp. 12846-12851, vol. 97, No. 23.
C. Andersson et al., "Transplantation of cultured type 1 astrocyte cell suspensions into young, adult and aged rat cortex: cell migration and survival", Int. J. Dev. Neurosci, 1993, pp. 555-568, vol. 11, No. 5.
X. Bao et al., "Functional Expression in *Xenopus oocytes* of Gap-junctional Hemichannels Formed by a Cysteine-less Connexin 43", The Journal of Biological Chemistry, 2004, pp. 9689-9692, vol. 279, No. 11.
P. Baril et al., "Periostin promotes invasiveness and resistance of pancreatic cancer cells to hypoxia-induced cell death: role of the $\beta_4$ integrin and the PI3k pathway", Oncogene, 2007, pp. 2082-2094, vol. 26.
A. Björklund, "Better cells for brain repair", Nature, 1993, pp. 414-415, vol. 362.
D. Bourbeau et al., "Suicide gene therapy with an adenovirus expressing the fusion gene CD::UPRT in human glioblastomas: different sensitivities correlate with $p_{53}$ status", The Journal of Gene Medicine, 2004, pp. 1320-1332, vol. 6.
A. B. Brown et al., "Intravascular Delivery of Neural Stem Cell Lines to Target Intracranial and Extracranial Tumors of Neural and Non-Neural Origin", Human Gene Therapy, 2003, pp. 1777-1785, vol. 14.
G-L. Defer et al., "Long-term outcome of unilaterally transplanted parkinsonian patients", Brain, 1996, pp. 41-50, vol. 119.
K. B. Frank et al., "Interaction of Herpes Simplex Virus-induced DNA Polymerase with 9-(1,3-Dihydroxy-2-propoxymethyl) guanine Triphosphate", The Journal of Biological Chemistry, 1984, pp. 1566-1569, vol. 259, No. 3.
C. R. Freed et al., "Survival of Implanted Fetal Dopamine Cells and Neurologic Improvement 12 to 46 Months after Transplantation for Parkinson's Disease", The New England Journal of Medicine, 1992, pp. 1549-1555, Vo. 327, No. 22.

(Continued)

*Primary Examiner* — Blaine Lankford
*Assistant Examiner* — David Berke-Schlessel
(74) *Attorney, Agent, or Firm* — Hershkovitz & Associates, PLLC; Abraham Hershkovitz; Eugene Rzucidlo

(57) ABSTRACT

A novel use of periostin, and more particularly a composition for inducing the migration of neural stem cells, which contains periostin or a periostin-secreting cell as an active ingredient, based on the discovery of a novel function of periostin that induces the migration of neural stem cells. Periostin induces the migration of neural stem cells, and thus the composition for inducing the migration of neural stem cells, which contains periostin or periostin-secreting cells as an active ingredient, can be used in various applications based on neural stem cells. A pharmaceutical composition containing suicide gene-expressing neural stem cells and periostin allows the neural stem cells to effectively migrate to tumor tissues, and thus can be used as a cell therapeutic agent for treating cancer. Also, the pharmaceutical composition containing neural stem cells and periostin has improved effects on the stimulation of regeneration of nerve cells and the treatment of neural diseases.

2 Claims, 15 Drawing Sheets

(56) References Cited

OTHER PUBLICATIONS

F. H. Gage, "Mammalian Neural Stem Cells", Science, 2000, pp. 1433-1438, vol. 287.
L. Gillan et al, "Periostin Secreted by Epithelial Ovarian Carcinoma Is a Ligand for $\alpha_v\beta_3$ and $\alpha_v\beta_5$ Integrins and Promotes Cell Motility", Cancer Research, 2002, pp. 5358-5364, vol. 62.
C. B. Johansson et al., "Identification of a Neural Stem Cell in the Adult Mammalian Central Nervous System", Cell, 1999, pp. 25-34, vol. 96.
PW Johnson et al., "Function of gingival fibroblasts and periodontal ligament cells in the presence of methyl mercaptan", 1999.
U. J. Kang et al., "Regulation of Dopamine Production by Genetically Modified Primary Fibroblasts", The Journal of Neuroscience, 1993, pp. 5203-5211, vol. 13, No. 12.
R. Kanno et al, "Epigenetic regulator polycomb group protein complexes control cell fate and cancer", Cancer Sci., 2008, pp. 1077-1084, vol. 99, No. 6.
J. H. Kordower et al., "Neuropathological Evidence of Graft Survival and Striatal Reinnervation after the Transplantation of Fetal Mesencephalic Tissue in a Patient with Parkinson's Disease", The New England Journal of Medicine, 1995, pp. 1118-1124, vol. 332, No. 17.
H. A. Lindner et al., "The Papain-Like Protease from the Severe Acute Respiratory Syndrome Coronavirus Is a Deubiquitinating Enzyme", Journal of Virology, 2005, pp. 15199-15208, vol. 79, No. 24.
J. J. Lopez-Lozano et al., "Regression of Parkinsonian Fetal Ventral Mesencephalon Grafts Upon Withdrawal of Cyclosporine A Immunosuppression", Transplantation Proceedings, 1997, pp. 977-980, vol. 29.
K. Nakamura et al., "Antitumor effect of genetically engineered mesenchymal stem cells in a rat glioma model", Gene Therapy, 2004, pp. 1155-1164, vol. 11.
M. Niethammer et al., "NUDEL Is a Novel Cdk5 Substrate that Associates with LISI and Cytoplasmic Dynein", Neuron, 2000, pp. 697-711, vol. 28.
L. Olson, "Regeneration in the adult central nervous system: Experimental repair strategies", Nature Medicine, 1997, pp. 1329-1335, vol. 3, No. 12.
H. V. Praag et al., "Functional neurogenesis in the adult hippocampus", Nature, 2002, pp. 1030-1034, vol. 415.
J. M. Rosenstein, "Why Do Neural Transplants Survive?", Experimental Neurology, 1995, pp. 1-6, vol. 133.
P. R. Sanberg et al., "Testis-derived Sertoli cells have a trophic effect on dopamine neurons and alleviate hemiparkinsonism in rats", Nature Medicine, 1997, pp. 1129-1132, vol. 3, No. 10.
M. Sasaki et al., "Transplantation of an Acutely Isolated Bone Marrow Fraction Repairs Demyelinated Adult Rat Spinal Cord Axons", Glia, 2001, pp. 26-34, vol. 35, No. 1.
R-G. Shao et al., "Abrogation of Chk1-mediated S/G2 checkpoint by UCN-01 enhances ara-C-induced cytotoxicity in human colon cancer cells", Acta Pharmacol Sin, 2004, pp. 756-762, vol. 25, No. 6.
D. D. Spencer et al., "Unilateral Transplantation of Human Fetal Mesencephalic Tissue into the Caudate Nucleus of Patients with Parkinson's Disease", The New England Journal of Medicine, 1992, pp. 1541-1548, vol. 327, No. 22.
Y. Tang et al., "In Vivo Tracking of Neural Progenitor Cell Migration to Glioblastomas", Human Gene Therapy, 2003, pp. 1247-1254, vol. 14.
D. Turner et al., "Scientific and Ethical Concerns in Neural Fetal Tissue Transplantation", Neurosurgery, 1993, pp. 1031-1037, vol. 33, No. 6.
W. Yan et al., "Transduction of a Mesenchyme-specific Gene Periostin into 293T Cells Induces Cell Invasive Activity through Epithelial-Mesenchymal Transformation", The Journal of Biological Chemistry, 2006, pp. 19700-19708, vol. 281, No. 28.
Z. Zhang et al., "In vivo magnetic resonance imaging tracks adult neural progenitor cell targeting of brain tumor", NeuroImage, 2004, pp. 281-287, vol. 23.
English Language Abstract of KR 10-2004-0013997 A.
English Language Abstract of KR 10-2006-0093269 A.
English Language Abstract of KR 10-2007-0036289 A.

* cited by examiner

COMPOSITION FOR INDUCING MIGRATION OF NEURAL STEM CELLS CONTAINING PERIOSTIN AS EFFECTIVE INGREDIENT

CROSS-REFERENCE TO RELATED APPLICATIONS

The present application claims priority under 35 U.S.C. 119 to Korean Patent Application No. 10-2010-0130889, filed on Dec. 20, 2010, the disclosure of which is expressly incorporated by reference herein in its entirety.

TECHNICAL FIELD

The present invention relates to the novel use of periostin, and more particularly to a composition for inducing the migration of neural stem cells, which contains periostin or periostin-secreting cells as an active ingredient, based on the discovery of a novel function of periostin that induces the migration of neural stem cells.

BACKGROUND ART

Brains can perform complex functions by generating a systemic neural network through a series of processes, including the division, differentiation, survival and death of neuronal stem cells and the formation of synapses. Such brains have a low ability to regenerate, compared to other organs, and thus damage to the brain can result in serious sequelae. Particularly, the occurrence of a tumor in the brain can cause significant damage to the brain, resulting in a significant reduction in the survival rate of the patient. The most effective conventional method for treating brain tumors is the resection of brain tumors by a surgical operation. However, depending on the type and location of brain tumor, it is impossible to perform a surgical operation, and complete resection of brain tumors by surgery presents a high risk of complications. In addition, in chemotherapy with anticancer drugs, administration of a high concentration of anticancer drugs is required due to the presence of the blood-brain barrier, thus causing serious side effects.

In attempts to overcome such problems, gene therapy methods have been proposed that use viruses to introduce genes, which inhibit the proliferation of cancer cells, directly into the cancer cells. However, it was actually impossible to introduce viruses even into a minute tumor or cancer tissue. Also, conventional methods, including viral surface modification and magnetic transfer techniques, had limitations in targeting minute cancer tissue. Additionally, the problems according to the immune toxicity of viruses are still raised.

In recent years, as the affinity of stem cells (including neural stem cells and mesenchymal stem cells) for brain tumors has been known, a possibility to stem cells as a gene delivery medium has been proposed (Aboody et al., *Proc. Natl. Acad. Sci. USA*, 97:12846, 2000; Brown et al., *Human Gene Therapy*, 14:1777, 2003; Tang et al., *Human Gene Therapy*,14:1247, 2003; Zhang et al., *NeuroImage*, 23:281, 2004; Nakamura et al., *Gene Therapy*, 11:1155, 2004; Zhang et al., *NeuroImage*, 23:281, 2004). Particularly, with respect to methods for treating brain tumors using such stem cells, it was reported that, when neural stem cells expressing cytosine deaminase (CD) that is the *E. coli* suicide gene were used to target glioma, excellent anticancer effects were shown (Aboody et al., *Proc. Natl. Acad. Sci. USA*, 97:12846, 2000; Brown et al., *Human Gene Therapy*, 14:1777, 2003). Also, Korean Patent Laid-Open Publication No. 10-2007-0036289 discloses a composition for treating cancer comprising mesenchymal stem cells expressing a suicide gene.

However, the above-described methods have a problem in that they are not effective for the treatment of cancer, because cancer cells are targeted at a low level. In addition, these methods are inefficient, because craniotomy should always be performed in order to introduce neural stem cells expressing a suicide gene. Meanwhile, the above-described literature showed only the affinity of stem cells for brain tumors, but did not present a method for delivering neural stem cells to brain tumor sites, based on the discovery of a substance that causes the affinity.

Meanwhile, periostin that is also called "OSF-2" is a protein originally isolated from osteoblasts and is known to be involved in the replacement, adhesion and spreading of osteoblasts (WO/2005/062055). It causes mature cardiac cells to divide, thus inducing the production of new cardiac cells. Also, it is known that periostin is tissue-specifically expressed in the periosteum and periodontal ligament and that the expression is regulated by TGF-beta (Johnson & Lancero, 1999). Also, the possibility of periostin as a cancer metastasis marker has been reported (Wei Wan & Rong Shao, *J. Biol. Chem.*, 281(28):19700, 2006). Periostin is known as a protein that is secreted from various cancer cells. Specifically, periostin has been reported to be secreted from small intestinal and colon cancer cells (Bao et al., 2004), breast cancer cells (Shao et al., 2004), lung cancer cells (Sasaki et al., 2001), pancreas cancer cells (Baril et al., 2007) and ovarian cancer cells (Gillan et al., 2002). Also, it was reported that the expression of periostin increased to facilitate the differentiation of endothelial cells in damaged cardiac tissue and the migration of endothelial cells to the damaged site (Lindner et al., 2005) and also that periostin is involved in the metastasis, invasion, propagation and survival of cancer cells (Kanno et al., 2008). However, it has not yet been reported that periostin has a function of inducing the migration of neural stem cells.

Accordingly, the present inventors have made extensive efforts to provide a substance for inducing the migration of neural stem cells so that a cell therapeutic agent for inducing cancer cell death can be prepared, which has enhanced efficiency, and can be used in studies on neural stem cells in various fields. As a result, the present inventors have found that periostain isolated from tumor tissue has the ability to induce the migration of neural stem cells, thereby completing the present invention.

DISCLOSURE OF INVENTION

Technical Problem

It is an object of the present invention to provide a composition for inducing the migration of neural stem cells, which contains periostin or periostion-secreting cells as an active ingredient.

Another object of the preset invention is to provide a pharmaceutical composition for treating cancer or neural disease, which contains periostin or periostin-secreting cells as an active ingredient.

Technical Solution

To achieve the above objects, the present invention provides a composition for inducing the migration of neural stem cells, which contains periostin or periostion-secreting cells as an active ingredient.

The present invention also provides a pharmaceutical composition for treating cancer diseases, the composition containing: (a) neural stem cells expressing a suicide gene; and (b) periostin or periostin-secreting cells.

The present invention also provides a composition for stimulating the regeneration of nerve cells and a pharmaceutical composition for treating neural disease, each composition containing: (a) neural stem cells; and (b) periostin or periostin-secreting cells.

Advantageous Effects

The present invention is based on the discovery of a novel function of periostin that induces the migration of neural stem cells, and it provides a composition for inducing the migration of neural stem cells, which contains periostin or periostin-secreting cells as an active ingredient.

The inventive composition for inducing the migration of neural stem cells can be used to treat cancer diseases using neural stem cells and to stimulate the regeneration of nerve cells and treat neural diseases. In addition, the composition of the present invention can be widely used in various applications based on neural stem cells.

BRIEF DESCRIPTION OF THE DRAWINGS

FIG. 15 is a set of photographs showing a slice in 2 weeks of treatment with 5-FC after different migration period, 7 days (A) or 10 days (B), following implantation of neural stem cells (F3-CD).

BEST MODE FOR CARRYING OUT THE INVENTION

Figure 1:
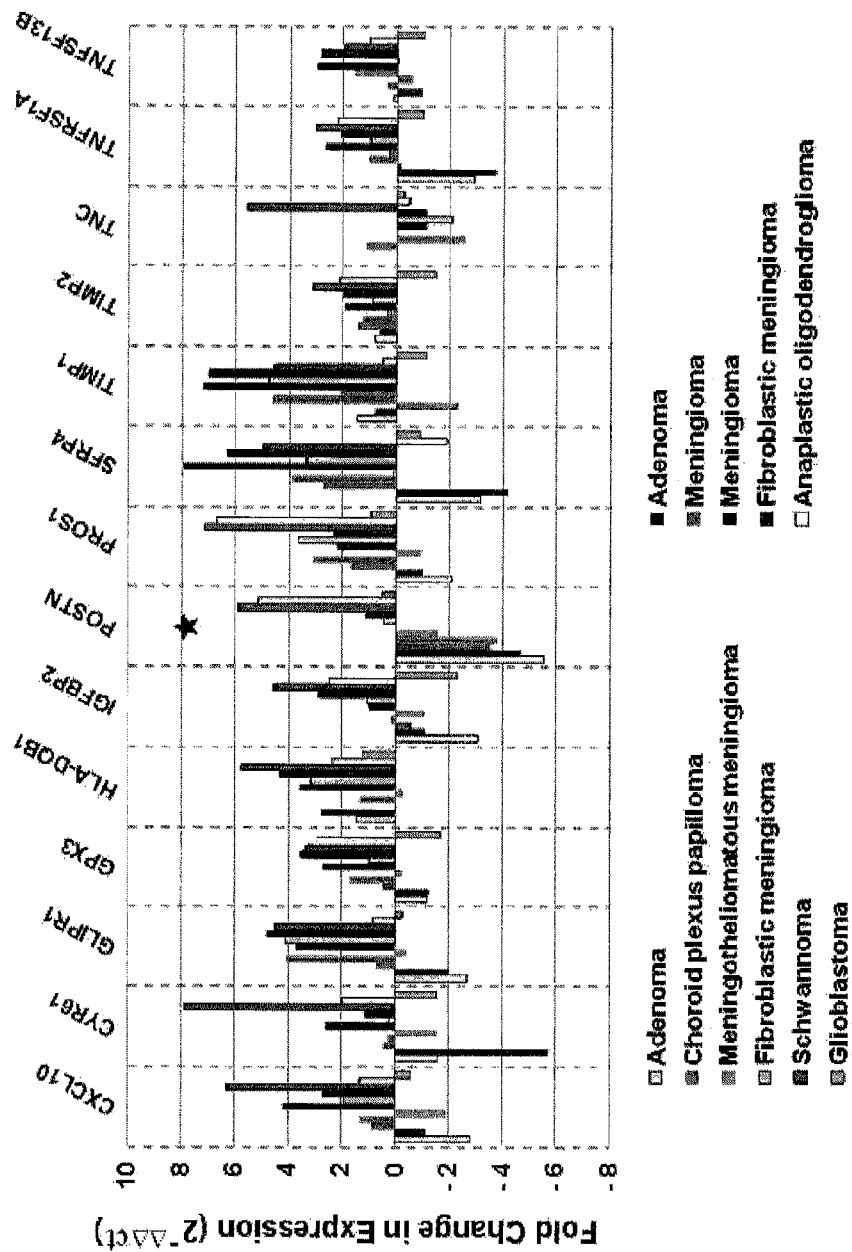
FIG. 1 is a graph showing the result of quantitative analysis of 14 candidate mRNAs for inducing migration of neural stem cells, which are overexpressed in tumor cells.

Unless otherwise defined, all technical and scientific terms used herein have the same meaning as commonly understood by one of ordinary skill in the art to which the invention pertains. Generally, the nomenclature used herein and the experiment methods which will be described later are well known and commonly used in the art.

The definition of main terms used in the detailed description of the invention is as follows.

As used herein, the term "stem cells" refers to cells having not only self-replication ability but also the ability to differentiate into at least two cells. The stem cells can be divided into totipotent stem cells, pluripotent stem cells, and multipotent stem cells.

As used herein, the term "neural stem cells" refers to stem cells having self-renewal ability, but also the ability to differentiate into neurons, oligodendrocytes and astrocytes, which are associated with nerve cells. In in vitro tests, such neural stem cells show characteristic cell clusters, called neurospheres, which are formed by reaction with nestin that is the marker of neural stem cells (Gage, F. H., *Science*, 287:1433, 2000).

As used herein, the term "suicide gene" refers to a gene having a function of converting a prodrug harmless to the human body into an anticancer substance toxic to malignant tumor cells. It allows stem cells having a suicide gene to target cancer cells, thus eliminating cancer. Herein, because stem cells having a suicide gene convert a prodrug into an anticancer substance, the suicide gene is harmless to normal cells and destroys only cancer cells, so that it can be efficiently used for cancer therapy.

In one aspect, the present invention is directed to a composition for inducing the migration of neural stem cells, which contains periostin or periostion-secreting cells as an active ingredient. In addition, the present invention includes a method of inducing the migration of neural stem cells using the composition for inducing the migration of neural stem cells.

In the present invention, periostin may comprise an amino acid sequence set forth in any one of SEQ ID NO: 1 to SEQ ID NO: 4, and may be a protein secreted from tumor cells. Periostin that is also called OSF-2 is a protein originally isolated from osteoblasts and is known to be involved in the replacement, adhesion and spreading of osteoblasts (WO/

2005/062055). Also, periostin is known as a protein which is overexpressed in tumor tissues, including lung cancer, ovarian cancer and breast cancer tissues (Wei Yan & Rong Shao, *J. Biol. Chem.*, 281(28), 19700-19708, 2006). In the present invention, it was found that periostin is overexpressed in brain tumor tissue.

It was found that periostin is expressed only in brain tumor tissue, but not in normal brain tissue. Particularly, it was found that periostin is overexpressed only in malignant tumors which have increased penetration into normal brain tissue and increase the recurrence rate of brain cancer after brain cancer surgery.

In the present invention, periostin-secreting cells may be cells that secrete periostin in natural conditions, that is, osteoblasts, etc. Preferably, the periostin-secreting cells may be cells obtained by introducing the periostin gene into general cells. In the present invention, a cell line introduced with the periostin gene was constructed by introducing a pCL-Ampho vector and a periostin-encoding pCXbsr-POSTN vector (Shiga University, Dr. Inoue) into 293T cells.

Also, an in vitro Boyden chamber assay revealed that periostin is a substance inducing the migration of neural stem cells. It was confirmed that the ability of periostin to induce the migration of neural stem cells is higher than that of VEGF known as a substance inducing the migration of stem cells, suggesting that periostin is an important factor in the induction of migration of stem cells. Also, it was found that the ability of periostin to induce the migration of neural stem cells was the highest at a concentration of 10 μg/ml. Meanwhile, the ability of periostin to induce the migration of neural stem cells was maintained over time.

In an in vivo test using animals, it was found that stem cells migrated toward cells overexpressing periostin and also that the number of migrated stem cells increased with the passage of time. This suggests that periostin can strongly induce the migration of stem cells in both in vivo and in vitro conditions.

The present inventors have found that neural stem cells have an αvβ5 integrin receptor and also that the migration of neural stem cells to tumor tissue is mediated by integrin αvβ5. This suggests that integrin αvβ5 is a primary receptor for periostin in neural stem cells and that periostin is an important ligand in inducing the migration of neural stem cells to tumor tissue.

The present inventors investigated the activation of the PI3K pathway (PI3K-AKT-mTOR-CDK5-Nudel1, PAK1) among signaling pathways which influence cells migration in order to examine what signaling pathway in neural stem cells are involved in inducing the migration of neural stem cells. In one Example of the present invention, it was found that the downward stages of the PI3K signaling pathway are activated depending on the time of treatment with periostin.

Meanwhile, in order to examine whether periostin is associated with the CDK5 signaling and MEK/ERK signaling pathway which mediate the migration of neural stem cells, cells were treated with periostin together with either PD98059 acting as an MEK/ERK kinase inhibitor or roscovitine acting as a cyclin-dependent kinase inhibitor. The effects of the inhibitors on cell migration were measured and, as a result, it was shown that the increase in cell migration by periostin was influenced by roscovitine, suggesting that the cell migration by periostin is mediated by the CDK5 pathway.

In addition, it is known that DCX which is the downstream signaling pathway of CDK5 is a factor regulating nucleokinesis during the migration of neural stem cells which is required to form the cerebral cortex in the developmental process of the brain. In order to examine whether the same signaling pathway is also involved in inducing the migration of neural stem cells by periostin, neural stem cells were treated with periostin. As a result, it was found that the location of DCX was shifted from cytoplasm to the area around the nucleus, suggesting that the DCX signaling pathway is also involved in inducing the migration of neural stem cells by periostin.

In another aspect, the present invention is directed to a pharmaceutical composition for treating cancer diseases, the composition containing: (a) neural stem cells expressing a suicide gene; and (b) periostin or periostin-secreting cells, and can be used for treatment of various kinds of cancer diseases, including brain tumor, lung cancer, breast cancer, ovarian cancer, and the like. In addition, the present invention is directed to a method for treating cancer diseases, the method including administering (a) neural stem cells expressing a suicide gene; and (b) periostin or periostin-secreting cells.

Also, the suicide gene is used for the purpose of killing cancer cells, it will be obvious to a person skilled in the art that the suicide gene can be replaced by any gene and factor known to inhibit the growth of cancer cells, for example, PEX, Trail, IFN-b, etc.

Examples of the suicide gene that is used in the present invention include Herpes simplex virus-thymidine kinase (HSV-TK), cytosine deaminase (CD) and the like.

In recent years, as methods of treating cancer by destroying tumor cells using suicide genes, systems consisting of various combinations of suicide genes and precursors have been reported. Among these methods, the most frequently used method uses a HSV-TK suicide gene and GCV (ganciclovir; 9-[(1,3-dihydroxy-2-propoxy)methyl]guanine). With respect to the HSV-TK/GCV system, it was reported that, when tumor cells are introduced with the HSV-TK gene and treated with GCV, the GCV inhibits the function of the DNA polymerase of the cells by the expressed HSV-TK or inserted into the cell DNA to interfere with DNA replication, thus causing necrosis of the cells (Frank et al., *J. Biol. Chem.*, 259:1566, 1984).

Also, cytosine deaminase has a function of converting 5-FC (5-fluorocytosine) into 5-FU (5-fluorouracil) that is a highly cytotoxic anticancer agent. For this reason, when 5-FU is systemically administered, it will cause serious side effects due to its high cytotoxicity, but when 5-FC is used together with a suicide gene, the concentration of 5-FU will increase only around the suicide gene, so that the anticancer effect of 5-FU will appear locally around cancer cells (Bourbeau et al., *J. Gene Med.*, 6:1320, 2004).

The suicide gene can be introduced into neural stem cells using a viral vector containing it, preferably a retroviral vector, according to any conventional method of introducing genes into cells. Specifically, the suicide gene can be introduced into neural stem cells by inserting the suicide gene into a retroviral vector to construct an expression vector, introducing the vector into packaging cells to prepare transformants, culturing the transformants, filtering the cultured transformants to obtain a retroviral solution, and infecting neural stem cells with the retroviral solution. Then, neural stem cells that continuously express the suicide gene can be collected using the selective marker contained in the retroviral vector.

In one Example of the present invention, it was found that, when periostin-secreting cells were introduced into a brain cancer site in a rat brain cancer model and when neural stem cells introduced with a suicide gene were introduced into the brain, the size of the rat brain cancer site decreased. Also, in the rat brain cancer model, it was found that, as the amount of periostin increased, the size of the brain cancer in the rat decreased. It is generally known that the patient's prognosis is a year or less even after a surgical operation due to the recurrence of malignant tumors caused by minute malignant tumor cells which cannot be found by existing methods. However, according to Examples of the present invention, it can be seen that, as the amount of periostin increases, the number of invasive malignant tumor cells which spread from the central portion of brain cancer to normal tissue significantly decreases. Thus, the use of the inventive pharmaceutical composition for treating cancer, which contains (a) neural stem cells expressing a suicide gene and (b) periostin or periostin-secreting cells, will make it possible to inhibit the growth of a malignant tumor and inhibit the metastasis of a malignant tumor to normal surrounding tissue, thereby preventing the recurrence of a malignant tumor.

It will be obvious to a person skilled in the art that, when the inventive pharmaceutical composition for treating cancer, which contains (a) neural stem cells expressing a suicide gene and (b) periostin or periostin-secreting cells, is injected into the affected part using, for example, an osmotic pump, so that it is continuously secreted, the periostin will induce the migration of the neural stem cell so that the neural stem cell will migrate to a brain tumor cell in a more efficient manner than a conventional method and expresses the suicide gene therein, indicating that the composition of the present invention can be effectively used for the treatment of various cancer diseases, including brain tumor, lung cancer, breast cancer, ovarian cancer, and the like. Still another aspect, the present invention is directed to a composition for stimulating the regeneration of nerve cells and a pharmaceutical composition for treating neural disease, each composition containing: (a) neural stem cells; and (b) periostin or periostin-secreting cells. The periostin-secreting cell in the present invention may be any cell type present in the body, and may preferably be a nerve cell. In addition, the present invention is directed to a method for treating neural disease, the method including administering periostin or periostin-secreting cells. Preferably, neural stem cells may be further administered.

In the present invention, the term "neural disease" is meant to include nerve injury, and examples of the neural disease include brain disease, peripheral nerve injury, amyotropic lateral sclerosis and peripheral nerve disease. Herein, the "term "brain disease" is meant to include brain injury, and examples thereof include dementia, Parkinson's disease, Alzheimer's disease, Huntington's disease, epilepsy, paralysis, stroke, ischemic brain disease and degenerative brain disease.

A process in which stem cells develop and differentiate in an adult brain can be defined as a regeneration process (Johansson, C. B., et al., *Cell*, 96(1):25, 1999), and it is known that neural stem cells are divided into granulocytes which can differentiate into functional cells (van Praag, H, et al., *Nature*, 415:1031, 2002). In this sense, numerous studies focused on stimulating nerve regeneration by promoting the development and differentiation of neural stem cells has been conducted. In addition, methods for stimulating the regeneration of nerve cells are well known to a person skilled in the art, and examples thereof include a method of stimulating the differentiation of neural stem cells by overexpressing nerve growth factor, a method of administering a composition containing a substance for stimulating the differentiation of neural stem cells, for example, wogonin (for example, KR 10-2004-0013997), and a method of using neural stem cells introduced with a gene stimulating the regeneration and differentiation of neural stem cells (for example, KR 10-2006-0093269).

Thus, when nerve stem cells, preferably nerve stem cells introduced with, for example, a gene for stimulating the development and differentiation of neural stem cells as described above, are administered together with periostin or the periostin-secreting cells as disclosed in the present invention, the targeting property thereof will be improved to stimulate the regeneration of nerve cells in a tissue-specific manner. Specifically, the migration of neural stem cells will be increased by periostin, and when periostin or periostin-secreting cells are injected into a location requiring the regeneration of nerve cells, followed by introducing neural stem cells into the body, the neural stem cells will migrate toward the periostin so that the regeneration of nerve cells in the area injected with the periostin or the periostin-secreting cells will be stimulated. More preferably, when periostin is injected into the affected part using an osmotic pump or the like so that it is continuously secreted, the neural stem cells will migrate to the periostin-secreting area so that the regeneration of nerve cells in that area will be stimulated.

Meanwhile, because it is known that neural diseases are very difficult to treat and reverse, neurotransplantation has been used for the repair of injured nerve tissue and the recovery of the function thereof (Bjorklund, *Nature*, 362:414, 1993; Olson, *Nature Med.*, 3:1329, 1997; Spencer et al., *N. Engl. J. Med.*, 327:1541, 1992: Freed et al., *N. Engl. J. Med.*, 327:1549, 1992; Kordower et al., *N. Engl. J. Med.*, 332:1118, 1995; Defer et al., *Brain*, 119:41, 1996; Lopez-Lozano et al., *Transp. Proc.*, 29:977, 1997; Rosenstein, *Exp. Neurol.*, 33:106, 1995; Turner et al., *Neurosurg.*, 33:1031, 1993; Kang et al., *J. Neurosci.*, 13:5203, 1993; Andersson et al., *Int. J. Dev. Neurosci.*, 11:555, 1993; Sanberg et al., *Nature Med.*, 3:1129, 1997). For example, a series of human patients with Parkinson's disease have been treated by neurotransplantation of mesencephalic cells obtained from 6 to 9 week old abortuses of human fetuses (Spencer et al., *N. Engl. J. Med.*, 327:1541, 1992: Freed et al., *N. Engl. J. Med.*, 327:1549, 1992; Kordower et al., *N. Engl. J. Med.*, 332:1118, 1995; Defer et al., *Brain* 119:41, 1996; Lopez-Lozano et al., *Transp. Proc.*, 29:977, 1997). Thus, as described above, when periostin or periostin-secreting cells and neural stem cells are injected into the affected part, the neural stem cells will migrate to the periostin-secreting area so that the regeneration of nerve cells in that area can be stimulated, indicating that this ability to stimulate the regeneration of nerve cells can be used for the treatment of neural diseases.

In the present invention, the ability of periostin to induce the migration of neural stem cells was confirmed, and as described above, the method of regenerating nerve cells using neural stem cells and the effect thereof on the treatment of neural diseases were confirmed. Thus, it will be obvious to a person skilled in the art that, when neural stem cells are administered together with periostin or periostin-secreting cells, the neural stem cells will migrate to the area requiring nerve regeneration so that the regeneration of nerve cells can be stimulated in a tissue-specific manner, indicating that the administration of neural stem cells together with periostin or periostin-secreting cells is effective for the treatment of neural diseases.

The pharmaceutical composition of the present invention may be in the form of its pharmaceutically acceptable salts, and may also be used alone or in appropriate association, as well as in combination with other pharmaceutically active compounds.

The pharmaceutical composition according to the present invention may be formulated in the form of oral dosage forms, such as powders, granules, tablets, capsules, suspensions, emulsions, syrup or aerosol, skin external agents, suppositories and sterile injectable solutions. Examples of carriers, excipients and diluents, which can be contained in the composition, include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium state and mineral oil.

The composition of the present invention may be formulated with commonly used diluents or excipients, such as fillers, extenders, binders, wetting agents, disintegrants, surfactants, etc. Solid formulations for oral administration include tablets, pills, powders, granules, capsules and the like, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents. Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, and the like can be used. As the base of the suppositories, witepsol, Macrogol, Tween 61, cacao butter, laurin fat, glycerogelatin and the like can be used.

The preferred dose of the composition of the present invention may vary depending on the condition and weight of the patient, severity of the disease, the form of drug, the route and period of administration, but can be appropriately selected by a person having ordinary skill in the art. However, for preferable effects, it is desirable to administer the composition of the present invention in an amount of 0.0001 to 500 mg/kg, and preferably 0.001 to 250 mg/kg, per day. Administration may be carried out once a day, or may be carried out several times a day. The amount of administration is not intended to limit the scope of the present invention in any way.

The most preferable method for administration of the composition of the present invention will be a method of administering periostin or periostin-secreting cells into the surgical area after tumor removal surgery to induce the migration of neural stem cells so as to stimulate the efficient removal of the remaining cancer cells.

The composition of the present invention can be administered by various routes to mammals, including rats, mice, domestic animals and humans. All modes of administration are contemplated, for example, administration can be made orally, rectally or by intravenous, intramuscular, subcutaneous, intracutaneous, intrauterine, epidural or intracerebroventricular injection.

EXAMPLES

Hereinafter, the present invention will be described in further detail with reference to examples. It will be obvious to a person having ordinary skill in the art that these examples are illustrative purposes only and are not to be construed to limit the scope of the present invention.

Particularly, only HB1.F3 and HB1.F5 were illustrated as neural stem cell lines in the following examples, but it will be obvious to a person skilled in the art that the use of other neural stem cells can provide the same results as the use of the illustrated cell lines.

Example 1

Isolation of Periostin and Examination of Tissue-specific Expression of Periostin 1-1: Isolation of Periostin Brain tumor tissues from three patients (obtained from the Ajou University Hospital, Korea; provided by M.D. K. Cho) as shown in Table 1 below were treated with Trizol reagent (Invitrogen) to extract total RNAs from the tumor tissues, thus preparing RNA samples. After the RNA sample has been extracted from each tissue by treatment with TRIzol, secreted genes which were highly expressed were examined using human U 133 Plus 2.0 GeneChip Oligo Microarrays (Affymetrix, Santa Clara, Calif., USA).

TABLE 1

| Tumor | Gender | Age | Histology | Up-regulated gene number | Down-regulated gene number |
| --- | --- | --- | --- | --- | --- |
| 1 | M | 32 | Glioma | 4491 | 3758 |
| 2 | F | 50 | Schwanoma | 4775 | 5087 |
| 3 | M | 63 | Ependyroma | 6119 | 6824 |

The examination results showed that a total of 14 candidates (CXCL10, CYR61, FN1, GLIPR1, GPX3, HLA-DQB1, POSTN, PROS1, SFRP4, TIMP1, TIMP2, TNC, TNFRSF1A and TNFSF13B) are genes which were more than 4-fold overexpressed in the tumor tissue compared to normal tissue and associated with to the process of tumor development (see Table 2)

TABLE 2

| | | | Fold change | | |
| --- | --- | --- | --- | --- | --- |
| Probe ID | Gene symbol | Gene Function | Tumor 1 | Tumor 2 | Tumor 3 |
| Hs.413924 | CXCL10 | lymphocyte trafficking | 3.76 | 3.16 | 4.27 |
| Hs.8867 | CYR61 | cell proliferation, angiogenic factor | 2.08 | 3.23 | 6.43 |
| Hs.553516 | GLIPR1 | cell proliferation, invasion, antiapoptic effect | 1.53 | 3.25 | 5.16 |
| Hs.386793 | GPX3 | antioxidative function | 3.16 | 2.97 | 5.20 |
| Hs.409934 | HLA-DQB1 | immune response | 2.08 | 6.51 | 6.96 |
| Hs.438102 | IGFBP2 | regulation of tumor growth and invasion | 5.04 | 1.66 | 6.07 |
| Hs.136348 | POSTN | induce cell migration and angiogenesis | 4.19 | 4.13 | 7.79 |
| Hs.64016 | PROS1 | Anti-coagulation | 3.84 | 2.19 | 8.00 |
| Hs.105700 | SFRP4 | inhibit cell proliferation | 2.74 | 3.37 | 4.83 |
| Hs.522632 | TIMP1 | Anti-apoptosis, induce cell growth | 2.25 | 2.26 | 4.38 |
| Hs.104839 | TIMP2 | Anti-angiogenesis | 2.32 | 2.07 | 3.38 |
| Hs.143250 | TNC | cell proliferation, migration | 2.15 | 7.21 | 3.87 |
| Hs.279594 | TNFRSF1A | Apoptosis | 2.80 | 2.32 | 2.68 |
| Hs.525157 | TNFSF13B | related with tumor genesis gene | 2.69 | 5.13 | 3.09 |

The resulting candidates were subjected to quantitative Real-Time PCR. For this purpose, total RNA (50 ng) was used to generate cDNA using Taqman Reverse Reagents (Applied Biosystems, Foster City, Calif., US).

Taqman Gene Expression assays which contained Taqman Universal PCR Master Mix and the primers (Applied Biosystems, US; see Table 3 below for Probe ID) of the 14 candidates and the positive control GAPDH were performed to analyze the PCR products. The PCR reactions were performed under the following conditions: 2 min at 50° C. for incubation; 10 min at 95° C. for AmpliTaq amplification and 40 cycles for the melting (95° C. for 15 sec) and annealing (60° C. for 1 min) steps. PCR reactions for each template were performed in one 96-well dish for one gene primer pair. The quantification of the expression of each gene was performed using the comparative CT method (Livak and Schmittgen, 2001), and the patient's brain tumor tissues (obtained from the Ajou University Hospital, Korea; provided by M.D. K. Cho) shown in Table 4 below were used.

TABLE 3

| Gene symbol | Probe ID |
| --- | --- |
| CXCL10 | Hs 00171042. m1 |
| CYR61 | Hs 00155479. m1 |
| FN1 | Hs 00415006. m1 |
| GLIPR1 | Hs 00199268. m1 |
| GPX3 | Hs 00173566. m1 |
| HLA-DQB1 | Hs 00109790. m1 |
| POSTN | Hs 00170815. m1 |
| PROS1 | Hs 00165590. m1 |
| SFRP4 | Hs 00180066. m1 |
| TIMP1 | Hs 00171558. m1 |
| TIMP2 | Hs 00234278. m1 |
| TNC | Hs 00233648. m1 |

TABLE 3-continued

| Gene symbol | Probe ID |
| --- | --- |
| TNFRSF1A | Hs 00533568. g1 |
| TNFSF13B | Hs 00198106. m1 |

TABLE 4

| Tumor | Gender | Age | Histology |
| --- | --- | --- | --- |
| Tumor1 | F | 59 | Adenoma |
| Tumor2 | F | 56 | Adenoma |
| Tumor3 | F | 36 | Choroidplexuspapilloma |
| Tumor4 | M | 36 | Meningotheliomatousmeningioma |
| Tumor5 | F | 48 | Meningioma |
| Tumor6 | M | 45 | Fibroblasticmeningioma |
| Tumor7 | F | 46 | Fibroblasticmeningioma |
| Tumor8 | F | 56 | Meningioma |
| Tumor9 | M | 63 | Schwannoma |
| Tumor10 | M | 45 | Anaplasticoligodendroglioma |
| Tumor11 | M | 33 | Glioblastoma |

As a result, as shown in FIG. 1, periostin (POSTN) was identified as a protein which was highly expressed (about 4-fold overexpressed) specifically in the malignant tumor tissue in comparison with the positive control GAPDH.

Meanwhile, the amino acid sequence of the overexpressed protein periostin was analyzed using the genetic information determined (http://www.ncbi.nlm.nih.gov/gene/10631) by search of NCBI Pubmed (http://www.ncbi.nlm.nih.gov/pubmed). As a result, the amino acid sequence of periostin having a total of the following four isoforms was determined.

```
periostin isoform 1
                                                                SEQ ID NO: 1
   1  mipflpmfsl  llllivnpin  annhydkila  hsrirgrdqg  pnvcalqqil  gtkkkyfstc 61  knwykksicg  qkttvlyecc  pgymrmegmk  gcpavlpidh  vygtlgivga  tttqrysdas 121  klreeiegkg  sftyfapsne  awdnldsdir  rglesnvnve  llnalhshmi  nkrmltkdlk 181  ngmiipsmyn  nlglfinhyp  ngvvtvncar  iihgnqiatn  gvvhvidrvl  tqigtsiqdf 241  ieaeddlssf  raaaitsdil  ealgrdghft  lfaptneafe  klprgvleri  mgdkvaseal 301  mkyhilntlq  csesimggav  fetlegntie  igcdgdsitv  ngikmvnkkd  ivtnngvihl 361  idqvlipdsa  kqvielagkq  qttftdlvaq  lglasalrpd  geytllapvn  nafsddtlsm 421  dqrllklilq  nhilkvkvgl  nelyngqile  tiggkqlrvf  vyrtavcien  scmekgskqg 481  rngaihifre  iikpaekslh  eklkqdkrfs  tflslleaad  lkelltqpgd  wtlfvptnda 541  fkgmtseeke  ilirdknalq  niilyhltpg  vfigkgfepg  vtnilkttqg  skiflkevnd 601  tllvnelksk  esdimttngv  ihvvdkllyp  adtpvgndql  leilnkliky  iqikfvrgst 661  fkeipvtvyt  tkiitkvvep  kikviegslq  piiktegptl  tkvkiegepe  frlikegeti 721  tevihgepii  kkytkiidgv  pveiteketr  eeriitgpei  kytristggg  eteetlkkll 781  qeevtkvtkf  ieggdghlfe  deeikrllqg  dtpvrklqan  kkvqgsrrrl  regrsq periostin isoform 2
                                                                SEQ ID NO: 2
   1  mipflpmfsl  llllivnpin  annhydkila  hsrirgrdqg  pnvcalqqil  gtkkkyfstc 61  knwykksicg  qkttvlyecc  pgymrmegmk  gcpavlpidh  vygtlgivga  tttqrysdas 121  klreeiegkg  sftyfapsne  awdnldsdir  rglesnvnve  llnalhshmi  nkrmltkdlk 181  ngmiipsmyn  nlglfinhyp  ngvvtvncar  iihgnqiatn  gvvhvidrvl  tqigtsiqdf 241  ieaeddlssf  raaaitsdil  ealgrdghft  lfaptneafe  klprgvleri  mgdkvaseal
```

-continued periostin isoform 3

```
                                                        SEQ ID NO: 3
  1  mipflpmfsl llllivnpin annhydkila hsrirgrdqg pnvcalqqil gtkkkyfstc
 61  knwykksicg qkttvlyecc pgymrmegmk gcpavlpidh vygtlgivga tttqrysdas
121  klreeiegkg sftyfapsne awdnldsdir rglesnvnve llnalhshmi nkrmltkdlk
181  ngmiipsmyn nlglfinhyp ngvvtvncar iihgnqiatn gvvhvidrvl tqigtsiqdf
241  ieaeddlssf raaaitsdil ealgrdghft lfaptneafe klprgvleri mgdkvaseal
301  mkyhilntlq csesimggav fetlegntie igcdgdsitv ngikmvnkkd ivtnngvihl
361  idqvlipdsa kqvielagkq qttftdlvaq lglasalrpd geytllapvn nafsddtlsm
421  dqrllklilq nhilkvkvgl nelyngqile tiggkqlrvf vyrtavcien scmekgskqg
481  rngaihifre iikpaekslh eklkqdkrfs tflslleaad lkelltqpgd wtlfvptnda
541  fkgmtseeke ilirdknalq niilyhltpg vfigkgfepg vtnilkttqg skiflkevnd
601  tllvnelksk esdimttngv ihvvdkllyp adtpvgndql leilnkliky iqikfvrgst
661  fkeipvtvyr ptltkvkieg epefrlikeg etitevihge piikkytkii dgvpveitek
721  etreeriitg peikytrist gggeteetlk kllqedtpvr klqankkvqg srrrlregrs
781  q
``` periostin isoform 4

```
                                                        SEQ ID NO: 4
  1  mipflpmfsl llllivnpin annhydkila hsrirgrdqg pnvcalqqil gtkkkyfstc
 61  knwykksicg qkttvlyecc pgymrmegmk gcpavlpidh vygtlgivga tttqrysdas
121  klreeiegkg sftyfapsne awdnldsdir rglesnvnve llnalhshmi nkrmltkdlk
181  ngmiipsmyn nlglfinhyp ngvvtvncar iihgnqiatn gvvhvidrvl tqigtsiqdf
241  ieaeddlssf raaaitsdil ealgrdghft lfaptneafe klprgvleri mgdkvaseal
301  mkyhilntlq csesimggav fetlegntie igcdgdsitv ngikmvnkkd ivtnngvihl
361  idqvlipdsa kqvielagkq qttftdlvaq lglasalrpd geytllapvn nafsddtlsm
421  dqrllklilq nhilkvkvgl nelyngqile tiggkqlrvf vyrtavcien scmekgskqg
481  rngaihifre iikpaekslh eklkqdkrfs tflslleaad lkelltqpgd wtlfvptnda
541  fkgmtseeke ilirdknalq niilyhltpg vfigkgfepg vtnilkttqg skiflkevnd
601  tllvnelksk esdimttngv ihvvdkllyp adtpvgndql leilnkliky iqikfvrgst
661  fkeipvtvyk piikkytkii dgvpveitek etreeriitg peikytrist gggeteetlk
721  kllqedtpvr klqankkvqg srrrlregrs q
```

1-2: Examination of Tissue-Specific Expression of Periostin

Whether the periostin isolated as described in Example 1-1 is expressed specifically in tumor tissue compared to normal brain tissue, the following experiment was performed.

Each of the patient's brain tumor tissue and normal brain tissue (obtained from the Ajou University Hospital) was fixed with a solution of 4% paraformaldehyde in 0.1M phosphate buffer, immersed in a solution of 30% sucrose in 0.1M phosphate buffer, allowed to stand overnight 4° C., and then frozen with an OCT compound. Each of the frozen samples was sectioned to 30 μm with a cryostat (KORF Instrum 900). The sectioned samples were washed with PBS, blocked with a solution of 5% goat serum and 0.5% triton X-100 in PBS for 30 minutes, and then washed twice with a solution of 0.5% BSA (bovine serum albumin) in PBS for 15 minutes. Then, each sample was treated with a 1:100 dilution of rabbit polyclonal human Periostin antibody (BioVender), incubated overnight at 4° C., and then incubated with biotin-conjugated secondary antibody at room temperature for 2 hours. After that, periostin of each sample was stained using an ABC kit (Vector) and a diaminbenzidin peroxidase (DAB) kit.

Figure 2:
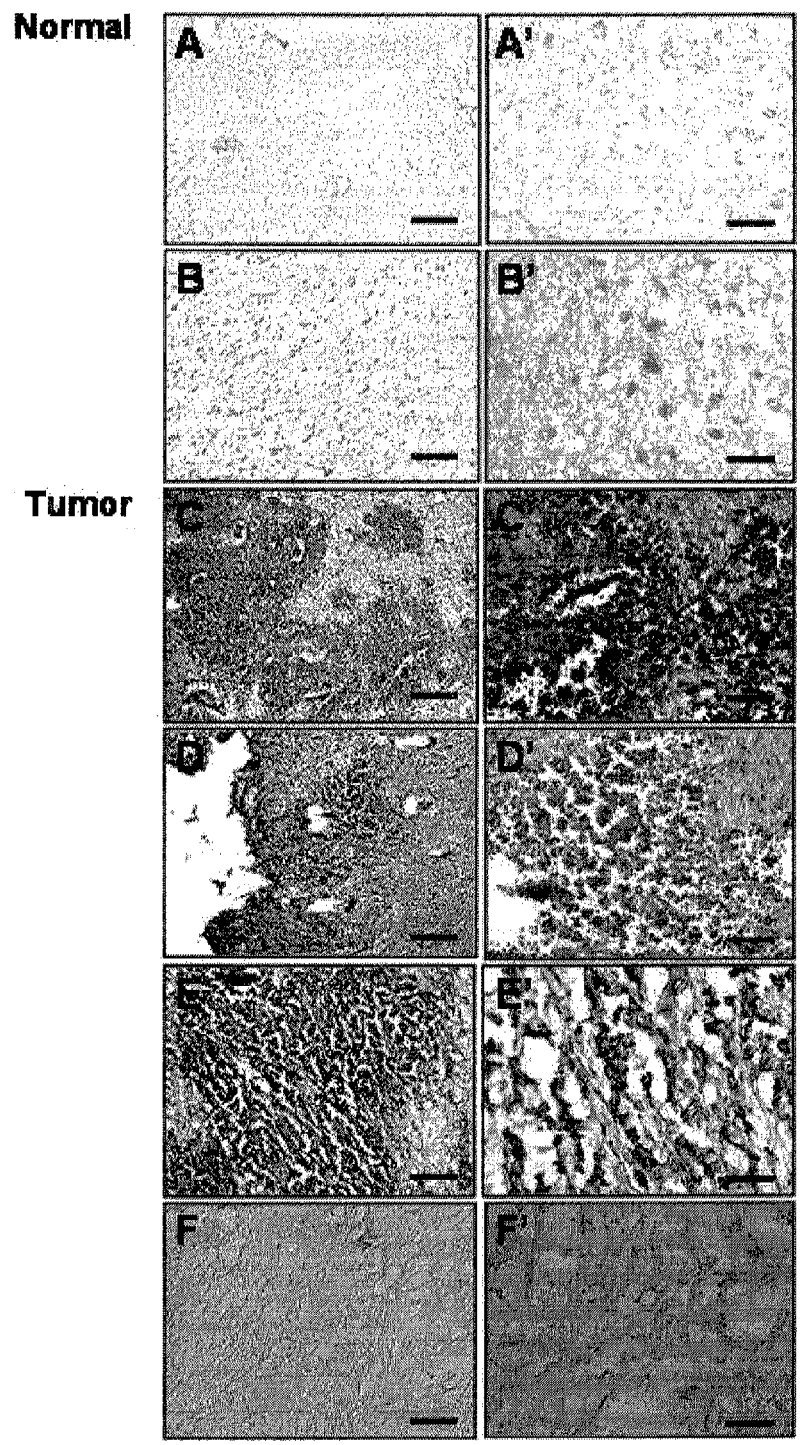
FIG. 2 is a set of optical microphotographs of normal brain tissue and brain tumor tissue, taken after immunostaining in order to determine whether periostin was expressed in the tissues.

As a result, as can be seen in FIG. 2, periostin was not expressed in the normal brain tissue, whereas it was expressed specifically in the brain tumor tissue. Particularly, it could be seen that the expression of periostin in the benign brain tumor was marked, and strongly appeared only in the malignant brain tissue, and such results were consistent with the real-time PCR results shown in FIG. 1. FIGS. 2A and 2B shows the results of observation of the normal brain tissue, FIGS. 2C to 2E show the results of observation of the malignant brain tumor tissue, and FIG. 2F shows the results of observation of the benign brain tumor tissue.

Example 2

Examination of the Ability of Periostin to Induce the Migration of Neural Stem Cells—in vitro 2-1 : Examination of Migration of Neural Stem Cells at Various Concentrations of Periostin In order to examine the effect of periostin on the migration of neural stem cells, a Boyden chamber assay was performed using two human neural stem cell lines (HB1.F3 and HB1.F5), thereby determining whether human neural stem cells migrated in response to periostin in vitro. For controls, VEGF (vascular endothelial growth factor) was used as a positive control, and FBS-DMEM medium was used as a negative control.

Specifically, cultured neural stem cells were detached with 0.05% trypsin, washed with DMEM medium, and then re-suspended in DMEM medium, after which $5\times10^4$ cells seeded into an upper chambers (Costar Transwell) in 200 μl of 10% FBS-containing DMEM medium. After one day, a lower chamber was treated with various concentrations of periostin or VEGF. The periostin was used at concentrations of 5, 10 and 20 μg/ml, and the VEGF was used at concentrations of 5, 10 and 20 ng/ml. 10% FBS-DMEM medium was used as a negative control. After 12 hours, in order to determine the number of cells that migrated from the upper chamber through a 8-μm porous polycarbonate membrane to the lower portion of the membrane in response to the stimulation of the lower chamber, the migrated neural stem cells were stained with hematoxylin and then counted.

Figure 3:
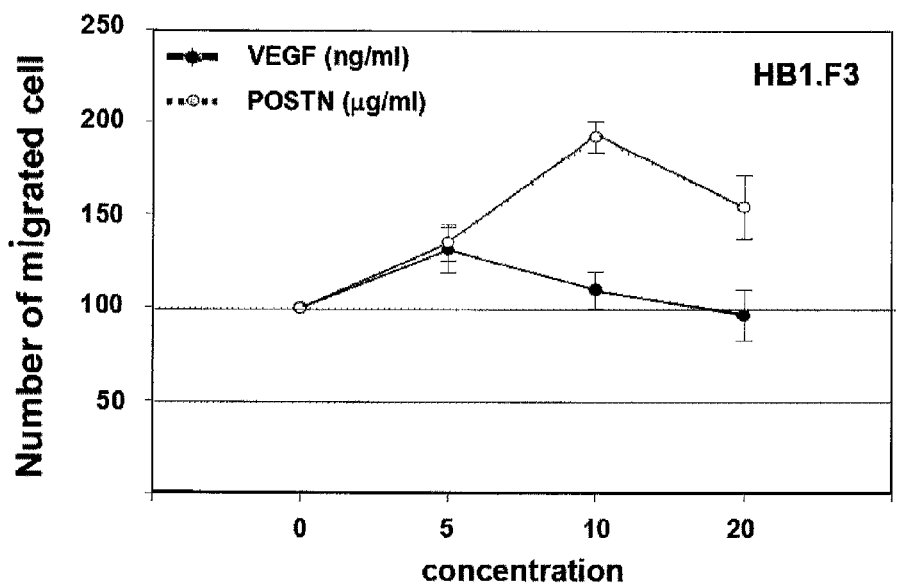
FIG. 3 is a set of graphs showing the results of measuring the number of neural stem cells, which migrated by periostin or VEGF, at various concentrations.
Figure 3:
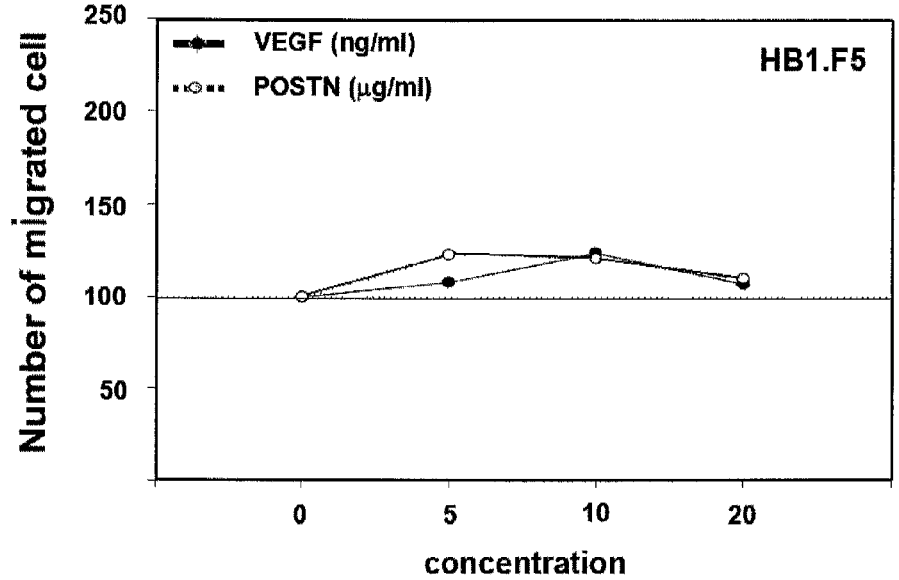

As a result, as can be seen in FIG. 3, it was observed that both the two neural stem cell lines migrated below the membrane in response to the periostin. As shown in FIG. 3A, in the case of the HB1.F3 cells treated with periostin, the ability to induce the migration of neural stem cells was increased by about 100% compared to when the HB1.F3 cells were not treated with periostin, and this increase was about 4 times higher than the increase in induction of migration by VEGF (25%), suggesting that the ability of periostin to induce the migration of neural stem cells is excellent compared to that of the positive control VEGF. Also, the ability of VEGF to induce the migration of neural stem cells was the highest at a concentration of 5 ng/ml, and the ability of periostin was the highest at a concentration of 10 μg/ml. In the case of the HB1.F5 cells, the ability to induce the migration of neural stem cells was similar between VEGF and periostin, but the migration of neural stem cells was increased upon treatment with periostin (FIG. 3B).

2-2: Examination of Migration of Neural Stem Cells at Various Time Points After Treatment with Periostin In order to demonstrate the migration-inducing ability of periostin by measuring the number of migrated cells, each of the two neural stem cell lines was detached with 0.05% trypsin, washed with DMEM medium, and then re-suspended in DMEM medium, after which $5\times10^4$ cells were inoculated into an upper chamber (Costar Transwell) in 200 μl of 10% FBS-containing DMEM medium. After one day, a lower chamber was treated with 10 μg/ml of periostin, and after 4 hours, 8 hours, 12 hours and 24 hours, the migrated cells were stained with H&E (hematoxylin & eosin), counted and photographed (Olympus BX51, Japan).

Figure 4:
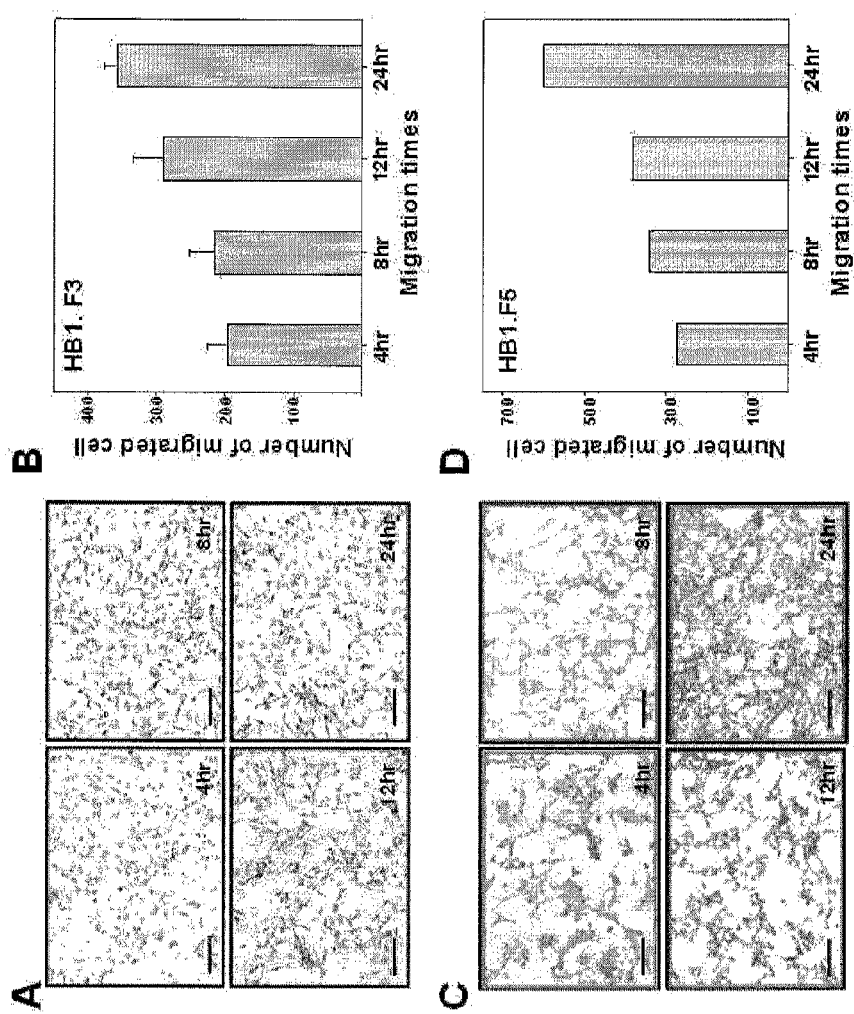
FIG. 4 is a set of graphs showing the results of measuring the number of neural stem cells, which migrated by periostin, at various time points.

As a result, as can be seen in FIG. 4, the two neural stem cell lines showed the same migration pattern with time, and the migration thereof was increased with time. As can be seen in the photographs of FIGS. 4A and 4C showing the staining results, the increase in the number of the migrated cells with the passage of time was clearly observed. In addition, the number of the migrated cells also increased (FIGS. 4B and 4D).

Example 3

Examination of Pathways Involved in the Migration of Neural Stem Cells by Periostin 3-1: Examination of Periostin Recognition Receptor Periostin is known to bind to a complex of integrin-alpha and integrin-beta, and a complex of integrin alpha V beta 3, alpha V beta 5 and alpha 6 beta 4 is known to act as a receptor in cell migration. In order to examine what complex acts as a receptor in the migration of HB 1.F3 neural stem cells, reverse transcription-PCR (RT-PCR) and a microarray assay were performed.

For RT-PCR, total RNA was isolated from F3 neural stem cells using TRIZol reagent (Invitrogen), and the first strand cDNA was synthesized by incubating the total RNA in a reaction mixture containing Superscriptll (Invitrogen, Calif.) and 12-18mer oligo dT at 42° C. for 50 minutes, and then at 72° C. for 15 minutes. Then, PCR was performed using 50 μl of a PCR mix containing 5 μl of 10× PCR buffer, 1.5 mM $MgCl_2$, 0.2 mM deoxyribonucleoside-triphosphate, 50 pmol primer, 1U Tag DAN polymerase (Invirogen) and 150 ng of the cDNA as a template. The PCR reaction was performed under the following conditions: 25-30 cycles of 45 sec at 94° C., 45 sec at 55° C. and 45 sec at 72° C., and final extension at 72° C. for 10 min. Primer sequences for each integrin subunit are shown in Table 5 below.

TABLE 5

| Gene | Primer sequence | F/B | SEQ ID NO |
|---|---|---|---|
| Human integrin alpha V | 5'-ACT GGG AGC ACA AGG AGA ACC-3'<br>5'-CCG CTT AGT GAT GAG ATG GTC-3' | Forward<br>Backward | SEQ ID NO: 5<br>SEQ ID NO: 6 |
| Human integrin beta 1 | 5'-CTG CAA GAA CGG GGT GAA TG-3'<br>5'-CAC AAT GTC TAC CAA GCC C-3' | Forward<br>Backward | SEQ ID NO: 7<br>SEQ ID NO: 8 |
| Human integrin beta 2 | 5'-CAA GCT GGC TGA AAA CAA CA-3'<br>5'-ACT GCT CCT GGA TGC ACT CT-3' | Forward<br>Backward | SEQ ID NO: 9<br>SEQ ID NO: 10 |
| Human integrin beta 3 | 5'-AGA TGC GAA AGC TCA CCA GT-3'<br>5'-CCG TCA TTA GGC TGG ACA AT-3' | Forward<br>Backward | SEQ ID NO: 11<br>SEQ ID NO: 12 |
| Human integrin beta 4 | 5'-GCC TTC ACT TTG AGC ACT CC-3'<br>5'-CTG CTG TAC TCG CTT TGC AG-3' | Forward<br>Backward | SEQ ID NO: 13<br>SEQ ID NO: 14 |
| Human integrin beta 5 | 5'-AGC AGC TTC CAT GTC CTG AG-3'<br>5'-GAA GTT GCT GGT GAG CTT CC-3' | Forward<br>Backward | SEQ ID NO: 15<br>SEQ ID NO: 16 |
| Human integrin beta 6 | 5'-GAC TCC GGA AAC ATT CTC CA-3'<br>5'-CTG ACA GTC GCA GTT GCA TT-3' | Forward<br>Backward | SEQ ID NO: 17<br>SEQ ID NO: 18 |
| Human integrin beta 7 | 5'-AGC AAT GGC CTC TAC AGT CGC AGC-3'<br>5'-GCT TGG AGA GAA ACC CAG AAA GTC-3' | Forward<br>Backward | SEQ ID NO: 19<br>SEQ ID NO: 20 |
| Human integrin beta 8 | 5'-TTC ATC ATT TTC ATA GTT ACA TTC-3'<br>5'-CAT TAA GTG TTT AAA AAT CTT TTT-3' | Forward<br>Backward | SEQ ID NO: 21<br>SEQ ID NO: 22 |

The amplified PCR products were loaded onto 1% agarose gel and then electrophoreses, and the resulting bands were observed. A microarray assay was performed using a probe for each subunit according to the Trizol method. For this purpose, neuronal stem cells were treated with Trizol reagent (Invitrogen) to extract total RNA, thus preparing an RNA sample. After the RNA sample has been extracted, the expressions of integrin subunits were examined using human U 133 Plus 2.0 GeneChip Oligo Microarrays (Affymetrix, Santa Clara, Calif., USA).

Figure 5:
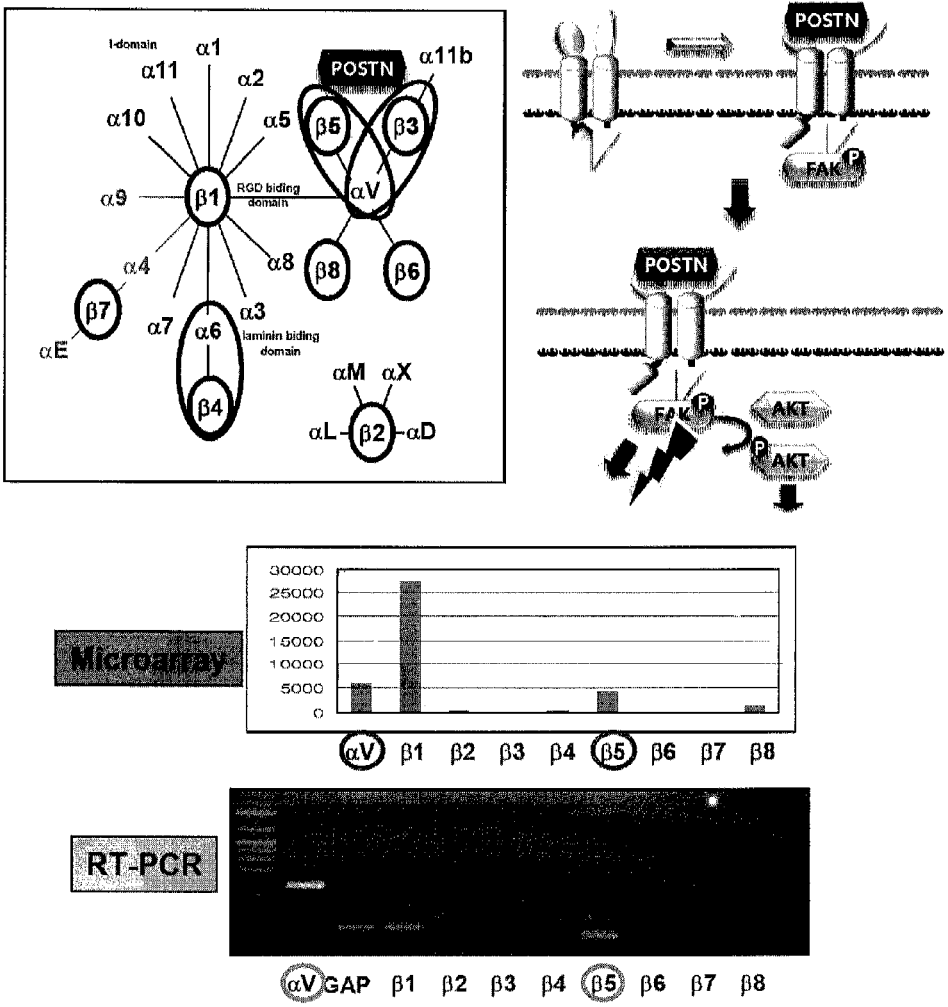
FIG. 5 shows the results of analyzing and quantifying the expression of integrin subunits in neural stem cells.

As a result, as shown in FIG. 5, among the subunits, integrin alpha V, beta 1 and beta 5 were highly expressed, and such results were consistent with the RT-PCR results. Thus, it was concluded that the receptor involved in the migration of neural stem cells is alpha V beta 5. Receptors for periostin include three types: integrin alpha V beta 3, alpha V beta 5, and alpha 6 beta 4. Among them, beta 3 and beta 4 do not exist, and thus alpha V beta 5 can be considered as a potential receptor for periostin.

3-2: Examination of Whether PI3 Kinase Signaling Pathway is Involved

The FAK signaling pathway is linked to kinases as its downstream pathways and transduces signals. With respect to cell migration, the PI3K/AKT signaling pathway (PI3K-AKT-mTOR-CDK5-Nudel1, PAK1) is frequently used as the downstream pathway of FAK, and thus the following experiment was performed in order to determine the kinase activation pathway.

First, neural stem cells treated with periostin were washed with PBS and lysed with PMSF and a protease inhibitor in RIPA buffer (0.5% sodiumdeoxycholate, 0.1% sodiumdodecyl sulfate, 1% NP-40, PBS). Protein concentration was determined by a Bio-Rad-DC protein assay (Bio-Rad, Hercules, Calif., US). The samples were adjusted to the same protein concentration, after 30 μg of each protein was separated on SDS-PAGE gel. Then, protein samples were transferred to an immobilon-P membrane (Millipore Corp., MA, US). For protein detection, the membrane was incubated in TBS-T 5% skim milk at room temperature for 30 minutes and washed three times with TBS-T for 15 minutes each time. Then, the membrane was incubated with primary antibodies of FAK, pFAK, PAK and pPAK (1:1000 dilution; Epitomics) in 5% BSA-TBS-T overnight at 4° C. Then, the membrane was washed three times with TBS-T for 15 minutes each time. Then, the membrane was incubated with secondary anti-rabbit antibody (1:2000 dilution; Zymed, Calif., USA) at room temperature for 1 hour. The membrane was washed three times with TBS-T, after which the antibody binding protein was added to an ECL Western blotting detection solution (Amersham Pharmacia Biotechnology, buckinghamahire, UK) for 1 minute and exposed to Kodak X-ray firm for detection. The Western blotting analysis was performed at various time points between 0 and 12 hours after treatment with periostin.

Figure 6:
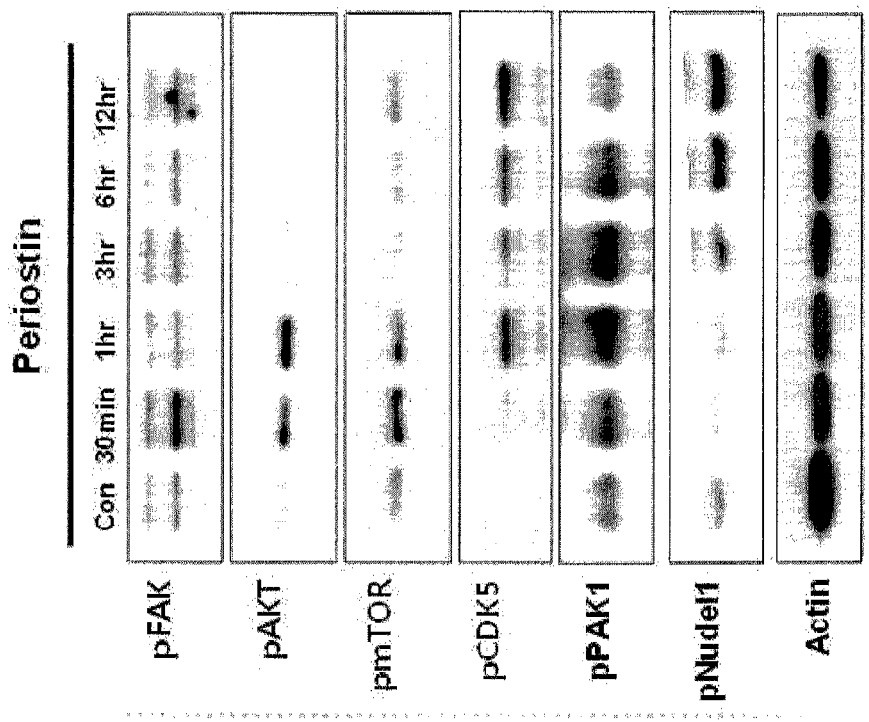
FIG. 6 shows the results of Western blotting for each step carried out in order to determine whether the induction of migration of neural stem cells by periostin is mediated by the PI3K signaling pathway.
Figure 6:
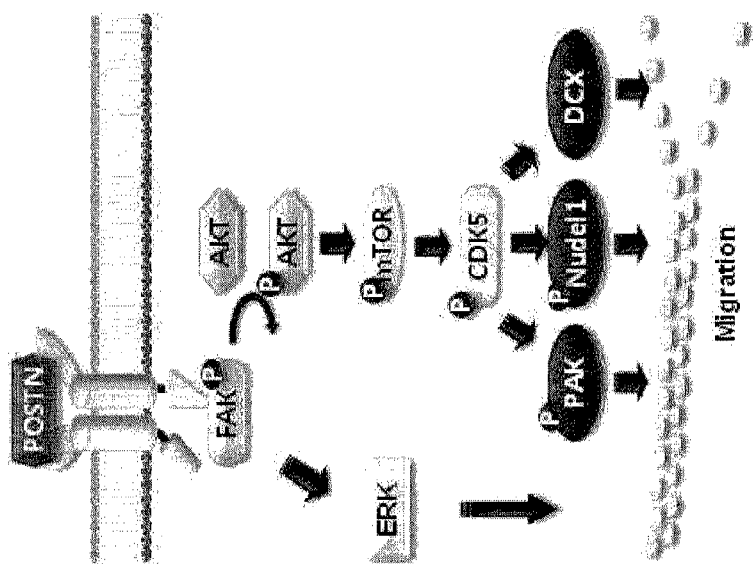

As can be seen in FIG. 6, the results of Western blotting indicated that FAK was highly activated from 30 minutes after treatment with periostin. Meanwhile, 1 hour after treatment with periostin, AKT and mTOR were activated, and then CDK5 was activated and the activation thereof was maintained up to 12 hours after treatment with periostin. Meanwhile, PAK1 started to be activated 1 hour after periostin treatment, and the activation thereof was maintained up to 6 hours. Nudel1 was activated at PAK1-activation decreased time point, and the activation thereof was maintained for 12 hours. Such results indicate that cell migration signaling induced by periostin is made through the FAK signaling pathway and occurs through the AKT signaling pathway and the downward pathway of CDK.

3-3: Examination of Nucleokinesis Induced by Periostin

DCX (doublecortin) together with Nudle1 and PAK1 is well known as a factor that regulates cell migration using actin and tubulin.

It has been reported that, in the development of the central nervous system, neural stem cells migrate from the subventricular zone to cortex through radial glial cells using the ERK (extracellular signal regulated kinase) and CDK5 signaling pathways, and in the neuronal migration, DCX participated in nucleus translocation, neucleokinesis (Niethammer et al., 2000). Thus, in order to examine the role of ERK, CDK5, and particularly DCX, in the migration of neural stem cells induced by periostin, neural stem cells were treated with the MEK/ERK inhibitor PD98057 or the CDK5 inhibitor roscovitine and subjected to an in vitro migration assay and an immunohistochemical assay as follows.

3-3-1: In vitro Migration Assay Using ERK Pathway and CDK5 Pathway Inhibitors

Cultured neural stem cells were detached with 0.05% trypsin, washed with DMEM medium and re-suspended in DMEM medium, after which $5 \times 10^4$ cells were inoculated into an upper chamber (Costar Transwell) in 200 μl of 10% FBS-containing DMEM medium. After one day, a lower chamber was treated with each of combined solution that composite with POSTN (R&D), VEGF, 20 nM PD98059 and 20 nM Roscovitine (Calbiochem).

After 12 hours, in order to determine the number of cells that migrated from the upper chamber through a 8-μm porous polycarbonate membrane to the lower portion of the membrane in response to the stimulation of the lower chamber, the migrated neural stem cells were stained with hematoxylin & eosin and counted.

Figure 7:
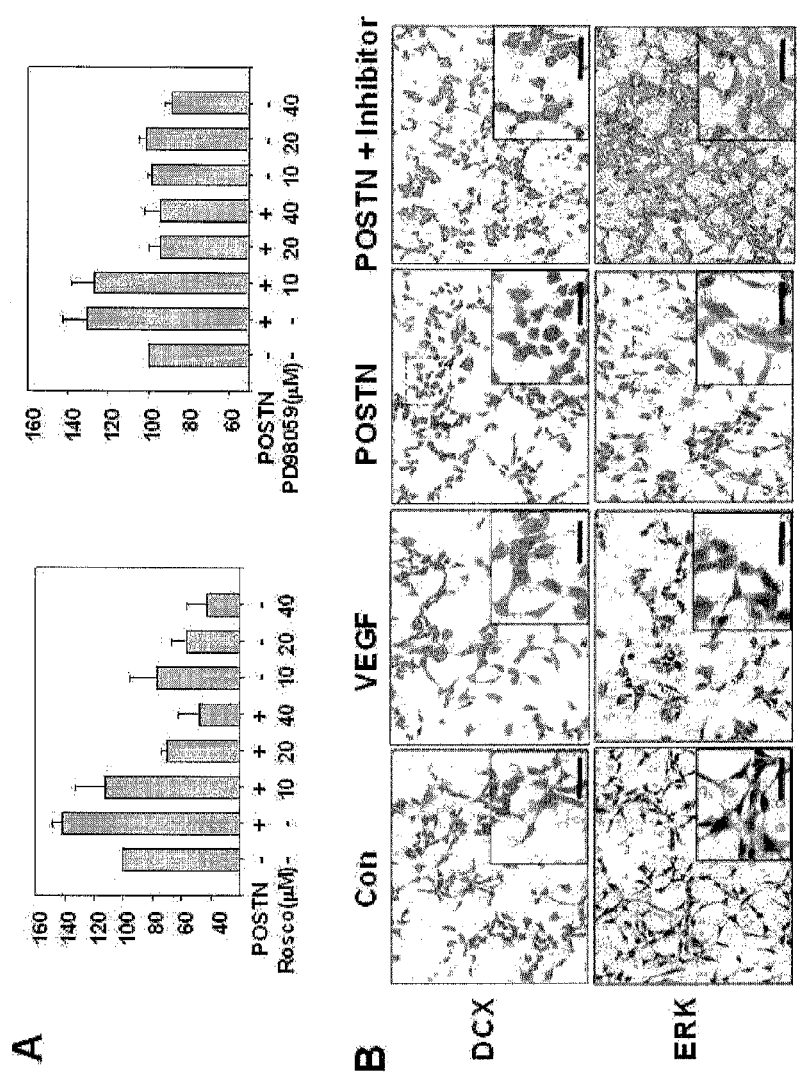
FIG. 7 shows the results of measuring the number of cells that migrated when treated with an MEK/ERK kinase inhibitor and a CDK5 inhibitor (FIG. 7A), and the locations and expression levels of DCX and ERK in the cells (FIG. 7B).

As a result, as can be seen in FIG. 7A, the migration of neural stem cells induced by periostin was significantly inhibited by roscovitine (94% inhibited) or PD98059 (40% inhibited). Also, in the control group not treated with periostin, the migration of neural stem cells was inhibited by roscovitine or PD98059, suggesting that the cell migration signaling induced by periostin passes through the ERK pathway and the CDK5 pathway. Particularly, it could be seen that the inhibitory effect of the ERK inhibitor PD98059 on the migration of neural stem cells was lower than that of the DCX inhibitor roscovitine. This indicates that the DCX signaling pathway plays an important role in the process of inducing the migration of neural stem cells by periostin.

3-3-2: Immunohistochemical Analysis of ERK and DCX

To analyze the ERK and DCX affection of migrated cells, transwell membrane immunostaining was performed using ERK and DCX antibodies (Cell signaling tech., Danver, Mass.).

Cultured neural stem cells were detached with 0.05% trypsin, washed with DMEM medium and re-suspended in DMEM medium, after which $5 \times 10^4$ neural stem cells were inoculated into an upper chamber (Costar Transwell) in 200 μl of 10% FBS-containing DMEM medium. After one day, a lower chamber was treated with each of VEGF (10 ng/ml), periostin (10 μg/ml) and periostin+inhibitor. After 12 hours, the changes in locations of DCX and ERK in the cells that migrated from the upper chamber through the 8-μm porous polycarbonate membrane to the lower portion of the membrane in response to the stimulation of the lower chamber were examined.

Next, the membrane was washed with PBS, blocked twice with a solution of 5% goat serum and 0.5% triton X-100 in PBS for 30 minutes, and then washed with a solution of 0.5% BSA (bovine serum albumin) in PBS for 15 minutes. After this, the membrane was incubated with a 1:500 dilution of goat polyclonal human DCX antibody and a 1:1000 dilution of rabbit polyclonal human ERK antibody at 4° C. overnight, and then washed twice with PBS for 15 minutes each time. Next, the membrane was incubated with biotin-conjugated anti-rabbit secondary antibody at room temperature for 1 hour and washed trice with PBS, after which periostin was detected by staining the membrane using an avidin-biotin kit (Vector, Calif.) and a diaminbenzidin peroxidase (DAB) kit (Vector, Calif.).

As a result, as can be seen in FIG. 7B, periostin and VEGF induced cell migration, and DCX was concentrated around the nuclei in the periotin-treated environment (see the small boxes of FIG. 7B). When the CDK5 inhibitor was added, the concentration of DCX around the nuclei was inhibited.

Example 4

Examination of the Ability of Periostin to Induce the Migration of Neural Stem Cells—In vivo 4-1: Construction of NIH3T3 Cell Line Overexpressing Periostin In order to construct a cell line overexpressing periostin, 293T cells were transfected with a pCL-Ampho vector expressing the amphotropic envelope gene and with a pCXbsr vector (Shiga University, Dr. Inoue) encoding the blasticidin S-resistant gene and the periostin gene, in which each of the vectors was digested with restriction enzymes in order to confirm whether the periostin gene and the amphotropic envelope gene were present in the vectors.

Figure 8:
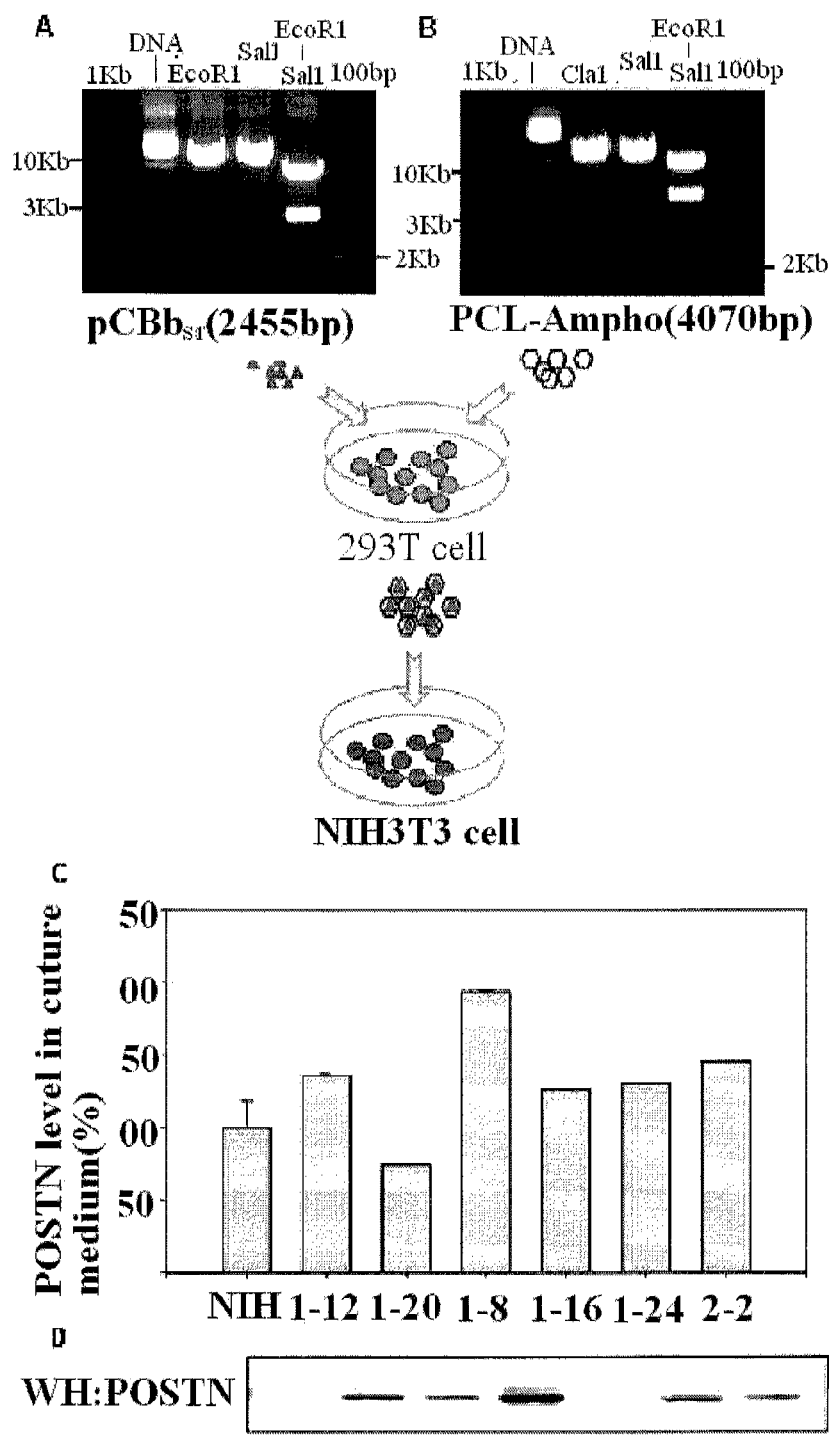
FIG. 8 shows a method for constructing a periostin-overexpressing cell line, and the results of analyzing vectors using restriction enzymes (FIGS. 8A and 8B), the results of ELISA assay (FIG. 8C), and the results of Western blotting (FIG. 8D).

Specifically, the two vectors were transfected with lipofectamin and Plus reagent (Invitrogen, Carlsbad, Calif.) according to the manufacturer's instructions. After 2 days, the culture medium was collected and treated with 5 μg/ml of blasticidin S (Invitrogen, Japan) for 1 week. Next, it was replaced with a fresh medium containing no blasticidin S and incubated for 3 days, after which the medium was incubated with NIH3T3 cells for 2 days. Then, a blasticidin S-containing medium was added thereto and incubated for 1-2 weeks, and cells introduced with the genes were selected. Cells forming colonies were culture in each well of a 96-well plate (FIGS. 8A and 8B).

The amounts of the secreted periostin in the recombinant periostin-expressing cell lines were analyzed by ELISA (FIG. 8C) and Western blotting (FIG. 8D), and the 1-8 cell line showing the highest expression level of periostin was selected and named "P-NIH3T3 cell line".

4-2: Ipsilateral Implantation of Neural Stem Cells and NIH3T3 Cells

Neural stem cells labeled with DiI were implanted into the cerebral hemispheric cortex ipsilaterally to the normal NIH3T3 cells or periostin-overexpressing NIH3T3 cells (P-NIH3T3) labeled with Dyecycle Green.

Specifically, $1 \times 10^6$ P-NIH3T3 cells labeled with Dyecycle green were implanted into the right striatum, and NIH3T3 cells were used as a control group. The location of implantation was AP +0.4, ML −2.3, DV −4.5 mm from the bregma. After 5 days, $1 \times 10^6$ neural stem cells labeled with DiI were implanted into the ipsilateral hemispheric cortex at a location of AP +0.4, ML −2.3, DV −2.0 from the bregma.

3 μl of HBSS (Hanks' balanced salt solution) or $1 \times 10^6$ P-NIH3T3 (periostin-overexpressing NIH3T3) cells labeled with Dyecycle Green were implanted into the right striatum. The location of implantation was AP +0.4, ML −2.3, DV −4.5 mm from the bregma. After 5 days, $1 \times 10^6$ neural stem cells labeled with DiI were implanted into the ipsilateral hemispheric cortex at a location of AP +0.4, ML −2.3, DV −2.0 from the bregma.

The cells and the HBSS were implanted at a rate of 0.2 µl/min using a 26-gauge Hamilton syringe (Hamilton, Nev., US) equipped with an automated microinjector (KD scientific INC, MA, US).

After implantation, the needle was maintained at that location for 15 minutes, and then pulled out slowly.

After 2-4 weeks, the rat's brain was fixed with 4% paraformaldehyde in 0.1M cold phosphate buffer. After 4 hours, the brain was immersed in 30% sucrose in 0.1M phosphate buffer, and then allowed to stand overnight at 4° C. Next, the brain was frozen using an OCT compound and sliced to 30 µm with a cryostat. The slice was mounted using Vectashield® Hard Set™ mounting medium (Vector, Calif., US) and measured using an Olympus IX71 confocal laser scanning microscope (Olympus, Tokyo, Japan).

Figure 9:
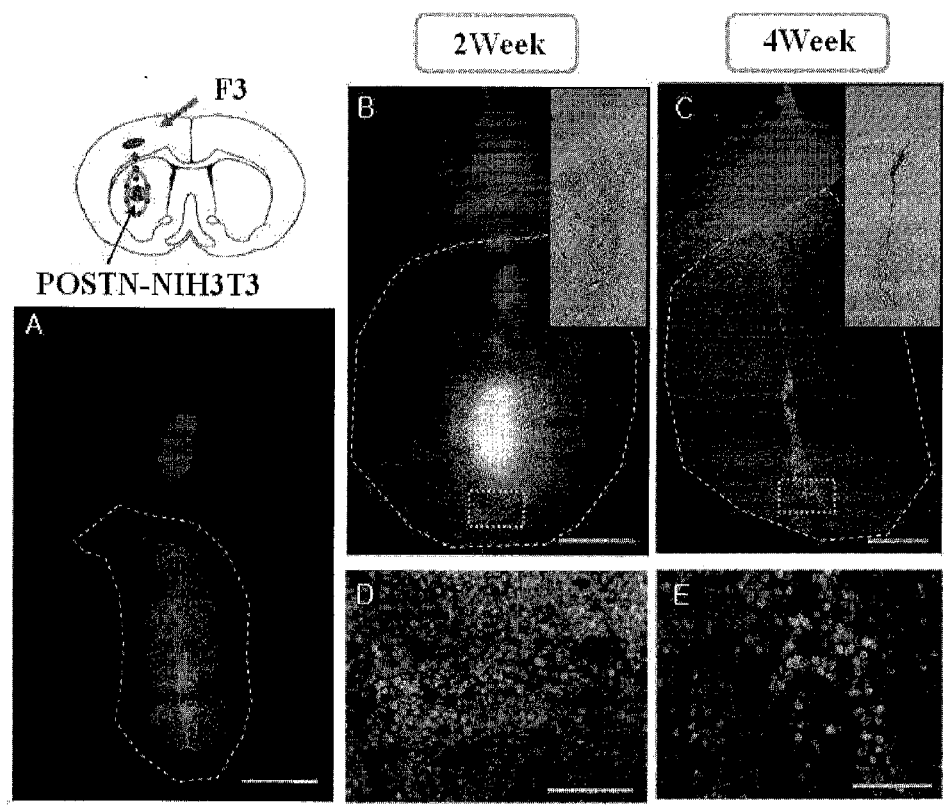
FIG. 9 is a set of confocal laser scanning microphotographs taken in order to observe the migration of fluorescent dye-labeled neural stem cells, implanted ipsilaterally, toward periostin-expressing cells with the passage of time, and schematically shows the portion into which the neural stem cells were introduced.

As a result, as shown in FIG. 9, the DiI-labeled neural stem cells showed no tropism for the normal NIH3T3 cells before 2 weeks after implantation. However, for the P-NIH3T3 cells continuously expressing periostin, it was observed that the neural stem cells passed through the corpus callosum to express the Vybrant Dyecycle Green label (FIG. 9B). 2 weeks after implantation of the neural stem cells, it was observed that the neural stem cells were dispersed throughout the P-NIH3T3 cells implanted around the striatum tissue and were mixed with the P-NIH3T3 cells (FIG. 9D). It was observed that the P-NIH3T3 cells continued to express periostin even 4 weeks after implantation of the neural stem cells and had the ability to induce migration of the neural stem cells (FIGS. 9C and 9E).

4-3: Contralateral Implantation of Neural Stem Cells and NIH3T3 Cells

DiI-labeled neural stem cells (HB1.F3) were implanted into the hemispheric cortex contralaterally to the hemispheric cortex implanted with periostin-overexpressing NIH3T3 cells (P-NIH3T3), in the same manner as Example 4-2, except that the location of implantation was AP +0.4, ML +2.3, DV −2.0 mm from the bregma.

As a result, it could be seen that the neural stem cells surrounded the p-NIH3T3 cells (FIGS. 10A and 10B) along the corpus callosum (FIG. 10C), even though the two types of cells were significantly spaced apart from each other. Also, it was observed that the neural stem cells migrated to the p-NIH3T3 cells along the corpus callosum pathway even 2 weeks after implantation of the cells (FIGS. 10F to 10H).

The in vivo expression of periostin was observed by immunohistochemical analysis using a DAB kit (diaminbenxidine peroxidase kit; Vecter, Calif.). Specifically, the slice was washed three times with PBS and blocked with a solution of 0.5% Triton X-100 and 5% BSA (bovine serum albumin) in PBS for 30 minutes. Then, the slice was washed with 0.5% BSA for 15 minutes and incubated with rabbit polyclonal human periostin antibody (1:500 duilution; Abcam, Cambridge, UK) overnight at 4° C. The slice was washed three times with PBS for 15 minutes each time and incubated with secondary anti-rabbit antibody (1:1000 dilution; Vector, Calif., US) at room temperature for 1 hours. Then, periostin was observed either by detection with a DAB kit (FIGS. 10D and 10I) or by fluorescence staining (FIGS. 10E and 10J).

Figure 10:
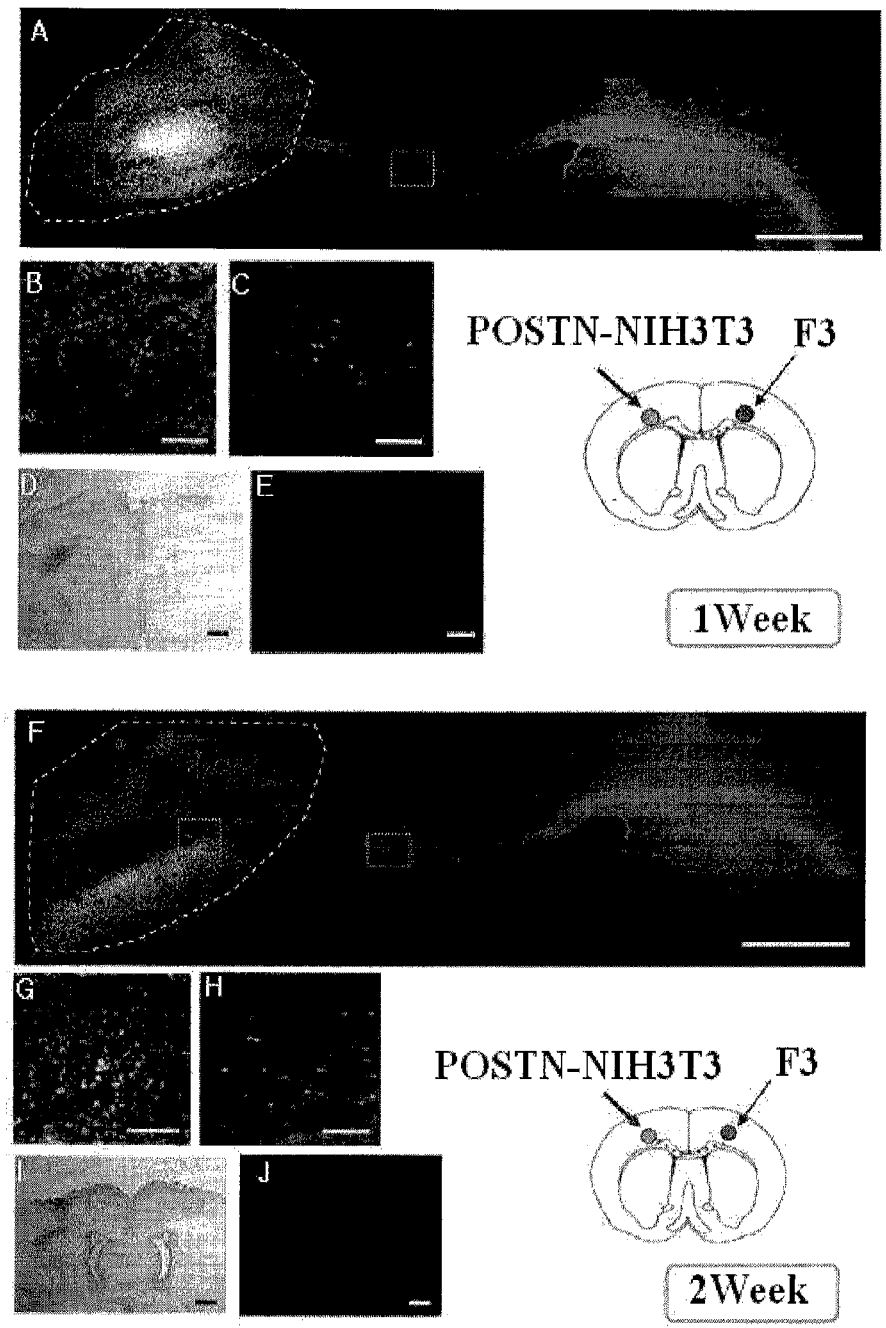
FIG. 10 is a set of confocal laser scanning microphotographs taken in order to observe the migration of fluorescent dye-labeled neural stem cells, implanted contralaterally, toward periostin-expressing cells with the passage of time, and schematically shows the portion into which the neural stem cells were introduced.

As can be seen in FIGS. 10D and 10I or from the fluorescence staining results (FIGS. 10E and 10J), the p-NIH3T3 cells continuously secreted periostin during 1-2 weeks after implantation. In the figures, the red color indicates neural stem cells, and the green color indicates p-NIH3T3 cells.

Example 5

Examination of Therapeutic Effects of Periostin-expressing Cells (p-NIH3T3) and Suicide Gene-expressing Cells (F3-CD) in Rat Glioma Model 5-1: Analysis of Cytotoxic Effect of F3-CD Cells 5-1-1: Determination of Whether F3-CD Cells Produce CD, and Analysis of Activity Thereof To determine the bystander effect of suicide gene-expressing neural stem cells on tumor cells, an F3-CD cell line expressing cytosine deaminase was made and whether the cell line expresses the CD gene and protein was determined.

For CD, the following primers were used.

```
SEQ ID NO: 23:
5'- GAGTCACCGCCAGCCACACCACGGC-3':    Forward

SEQ ID NO: 24:
5'- GTTTGTAATCGATGGCTTCTGGCTGC-3':   Backward
```

Total RNA was isolated from neural stem cells using TRIZol reagent (Invitrogen). The first strand cDNA was prepared by incubating a reaction mixture containing SuperscriptII (Invitrogen, Calif.), 12-18mer oligo dT and the isolated total RNA. Herein, the reaction mixture was incubated at 42° C. for 50 minutes, and then at 72° C. for 15 minutes. Next, PCR was performed using 50 µl of a PCR mix containing 5 µl of 10× PCR buffer, 1.5 mM $MgCl_2$, 0.2 mM deoxyribonucleotide-triphosphate, 50 pmol primer, 1U Tag DAN polymerase (Invirogen) and 150 ng of the cDNA as a template. The PCR reaction was performed under the following conditions: 25-30 cycles of 5 sec at 94° C., 60 sec at 60° C. and 90 sec at 72° C.; and final extension at 72° C. for 10 min.

Figure 11:
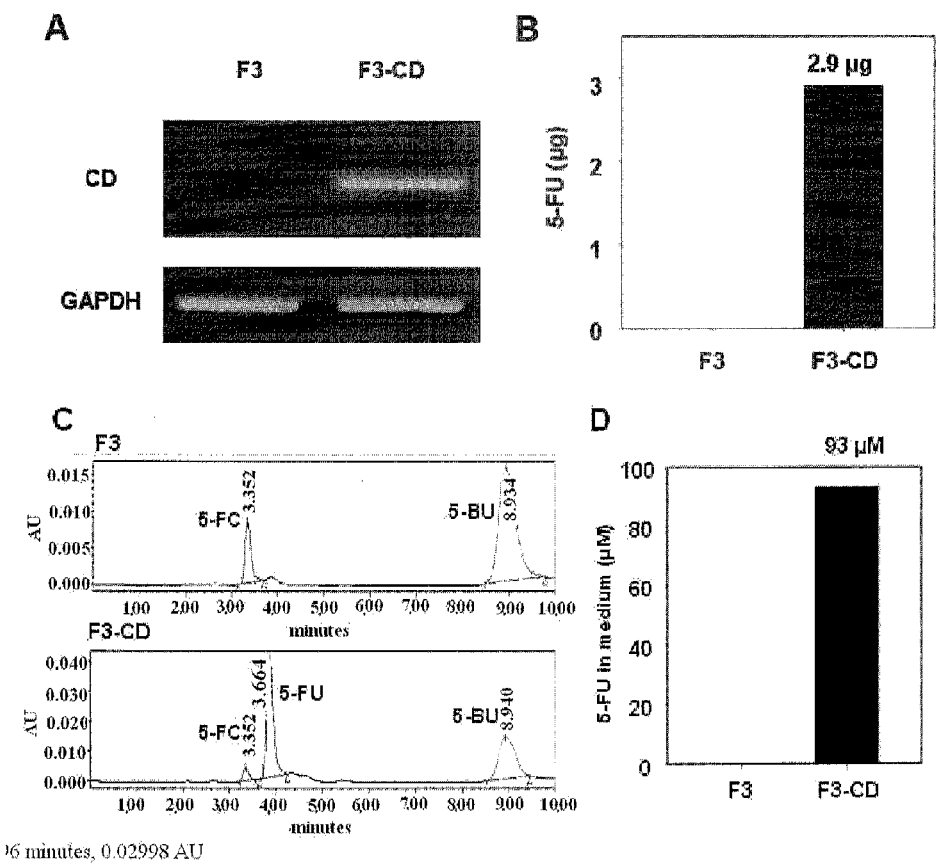
FIG. 11 shows the results of analyzing the expression levels of the CD gene in F3 cells and F3-CD cells (FIG. 11A), and the activity of the enzyme by HPLC analysis (FIGS. 11B to 11D).

The RT-PCR results showed clear bands. Thus, it could be seen that the CD gene was not expressed in the control F3 cell, but was expressed in the F3-CD cells (FIG. 11A).

5-1-2: HPLC Analysis of CD Protein

Through enzyme activity analysis and HPLC analysis, the activity of the CD protein was measured. The CD protein has the activity of converting 5-FC (5-fluorocytosine) into 5-FU (5-flurouracil) that is a highly toxic anticancer agent. For HPLC analysis, $2 \times 10^5$ F3-CD cells were dispensed into each well of a 12-well plate and cultured with 1 mM 5-FC in 1 ml of medium for 48 hours. 50 µl of the culture medium was extracted using 500 µl of a mixture of ethyl acetate: isopropanol: acetic acid (84:15:1 [v:v:v]), and the organic fraction was re-suspended in 500 µl of a mixture of water: methanol (4:1 [v:v]). HPLC of the resulting solution was performed using a Kromasil 100-5C-19 column (Kromasil, Bohus, Sweden) at 270 nm. 5-FC and 5-FU were separated at a flow rate of 1 ml/min by dissolution in 40 mM $KH_2PO_4$-containing isocratic mobile phase, adjusted to a pH of 7.0 by addition of 10% KOH. The residence time was 3.4 min for 5-FC, 3.9 min for 5-FU, and 8.9 min for 5-bromouracil (Sigma), and the quantitative analysis of 5-FC and 5-FU was performed using 5-bromouracil as an internal standard.

Meanwhile, 50 µg of the protein from the cell lysate was incubated at 37° C. for 8 hours in the presence of 1 mM 5-FC and subjected to HPLC analysis in the same manner as described above.

As a result, it was found that 2.9 µg of 5-FU was produced in the lysate by the CD and that the production of 5-FU was not observed in the control F3 cells (FIG. 11B). Also, the supernatant of the F3-CD cells cultured with 5-FC showed two peaks corresponding to 5-FC and 5-FU at an UV absorbance of 270 nm. Also, the quantification of HPLC showed 93 μM, indicating that the F3-CD cells convert 5-FC into 5-FU (FIGS. 11C and 11D). Accordingly, it was confirmed that the F3-CD cells encoding the CD gene can produce the CD protein having normal enzymatic activity and that the converted 5-FU is continuously accumulated in culture medium. It is considered the secreted 5-FU plays an important role in exhibiting a bystander effect for the surrounding cells.

5-1-3: Analysis of Cytotoxic Effect of F3-CD Cells on C6 Cells—in vitro

To determine the in vitro cytotoxic effect of F3-CD cells on rat glioma C6 cells (provided from Myung-Ae Lee, Ajou University) by co-culture of rat glioma C6 cells with F3-CD cells in the presence of 5-FC, the following experiment was performed.

Specifically, C6 cells and F3-CD cells were dispensed into each well of a 96-well plate at various ratios (C6:F3-CD=100: 5-200) and cultured for one day, after which the cells were cultured in 5-FC—containing fresh medium (100 μg/ml, Sigma). After 3 days, each well was washed with PBS, and MTT solution (0.5 mg/ml, Sigma) was added thereto. After 4 hours, the MTT was replaced with 200 μl of DMSO, and each well was further incubated for 1 hour. Then, the supernatant of each well was collected and transferred to a fresh 96-well plate, after which the number of the C6 cells was counted using a microplate spectrophotometer (Bio Tek instrument Inc.) at 550 nm and 630 nm as a reference filter.

Figure 12:
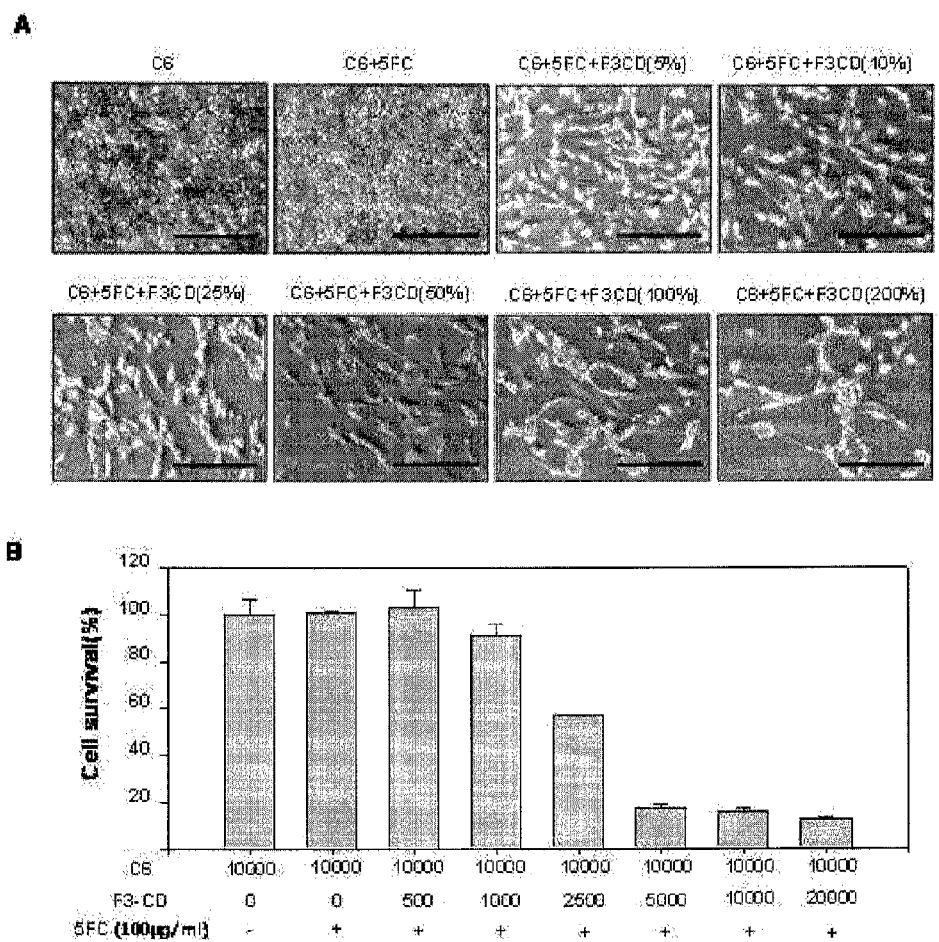
FIG. 12 is a set of photographs and graphs showing cell death around neural stem cells expressing a suicide gene (CD).

As a result, as can be seen in FIG. 12, as the number of F3-CD cells co-cultured with C6 cells was increased, the cytotoxic effect increased. Also, when the ratio of F3-CD cells to the total cells was 10%, C6 cells started to die, and when the ratio of F3-CD cells reached 50%, the death of 80% of C6 cells was induced.

5-2: Cytotoxic Effect of F3-CD Cells on p-NIH3T3 Cells—in vivo

In order to determine the bystander effect of F3-CD cells on p-NIH3T3 cells in in vivo conditions, the following bystander effect assay was performed.

$0.5-2\times10^6$ p-NIH3T3 cells labeled with Dyecycle green together with rat glioma C6 cells were implanted into the right striatum of rats. After 5 days, for each group, $1\times10^6$ neural stem cells labeled with DiI were implanted into the right hemispheric cortex. After implantation, the needle was allowed to stand for 15 minutes, and then was removed slowly. After 7-10 days, 5-FC was administered by intraperitoneal injection to the rats at different concentrations (250, 500 and 1000 μg/kg) everyday for 2 weeks.

Then, brains were collected from the rats and fixed with 4% paraformaldehyde in 0.1M cold phosphate buffer. After 4 hours, the brains were immersed in 30% sucrose in 0.1M phosphate buffer and allowed to stand overnight at 4° C. Then, the brains were frozen with an OCT compound and sliced to 30 μm with a cryostat. The slices were mounted using a gel mount (Biomeda corp, Foster City, Calif.). The cancer cells and the size thereof were measured using a BMF stereo investigator program (MicroBrightField Inc., Williston, USA).

Figure 13:
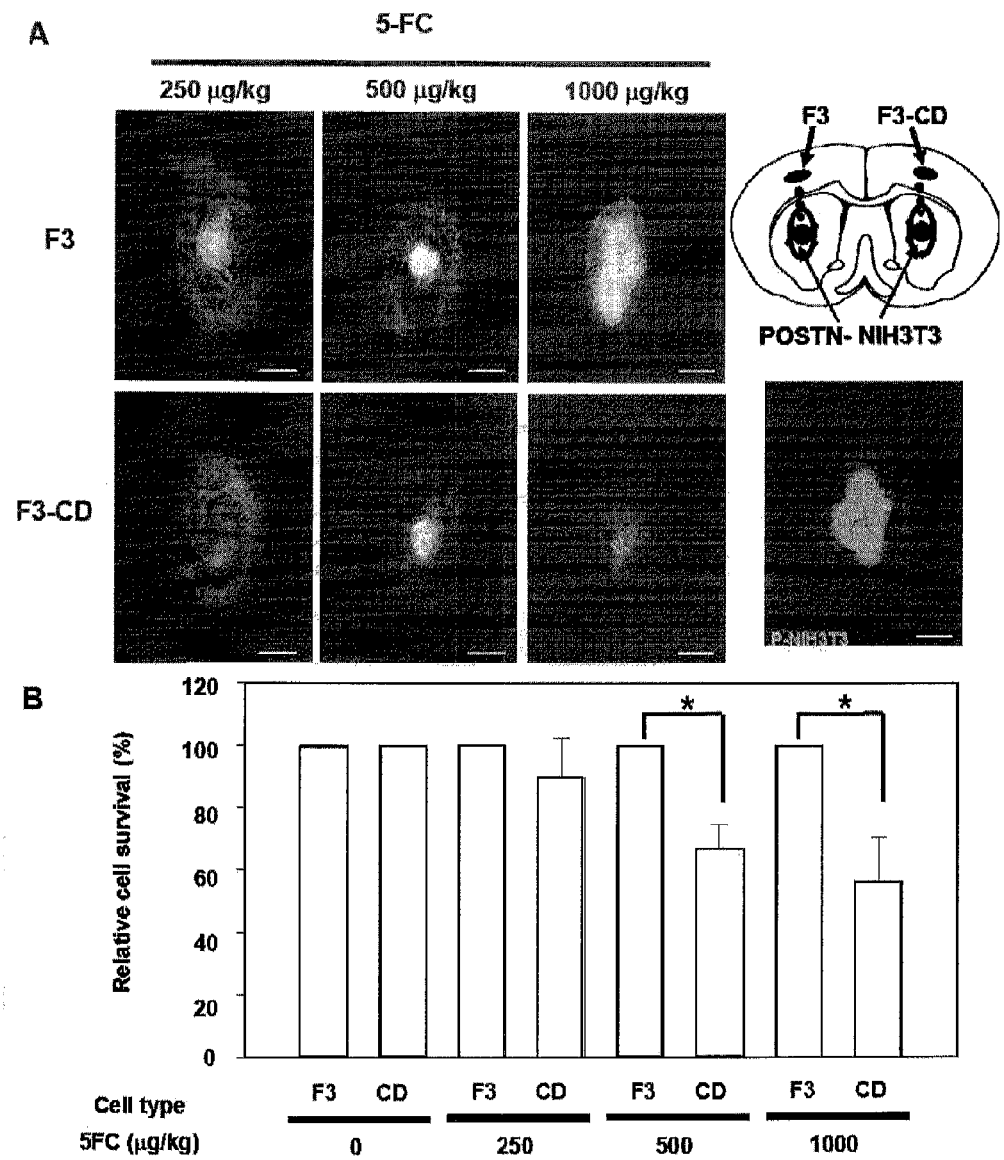
FIG. 13 is a set of photographs and graphs showing that suicide gene-expressing cells (F3-CD) implanted ipsilaterally into a rat brain were induced toward periostin-expressing cells and showed the in vivo bystander effect of killing the cells.

The survival rate of periostin-overexpressing NIH3T3 cells was stereologically measured. As a result, it was found that, when F3-CD cells were implanted into the animals having a high concentration of 5-FC, the survival rate of p-NIH3T3 cells was significantly decreased (44%; FIG. 13) compared to when the control F3 cells were implanted. The graph of FIG. 13B shows the results of quantifying the number of p-NIH3T3 cells in each rat (administered with 5-FC) using the stereo investigator program. In the in vivo assay, the bystander effect of the F3-CD cells seriously appeared in the group administered with 5-FC, particularly at a concentration of 500 μg/kg. Such results indicate that, even when F3-CD cell line and the periostin-overexpressing cell line are administered to different areas, the F3-CD cells migrates from the original area of implantation by periostin, so that the F3-CD cells exhibit sufficient cytoxicity on the periostin-overexpressing cells in vivo.

5-3: Examination of Therapeutic Effects of Periostin-expressing Cells (p-NIH3T3) and Suicide Gene-expressing Cells (F3-CD) in Rat Glioma Model In order to examine whether the use of periostin-expressing cells (p-NIH3T3) and suicide gene-expressing cells (F3-CD) can induce the death of cancer cells around the periostin-expressing cells to reduce the size of tumor tissue, thus exhibiting therapeutic effects, the following experiment was performed.

F3-CD cells, constructed in Example 4-1 and labeled with DiI, were implanted into the cerebral cortex of rats contralaterally to C6 glioma cells alone or a combination of C6 cells and p-NIH3T3 cells, and then treated with 5-FC for 2 weeks. Implantation of each type of cells was performed in the same manner as Example 4-3, and the rat brain was collected at the end of treatment with 5-FC.

Figure 14:
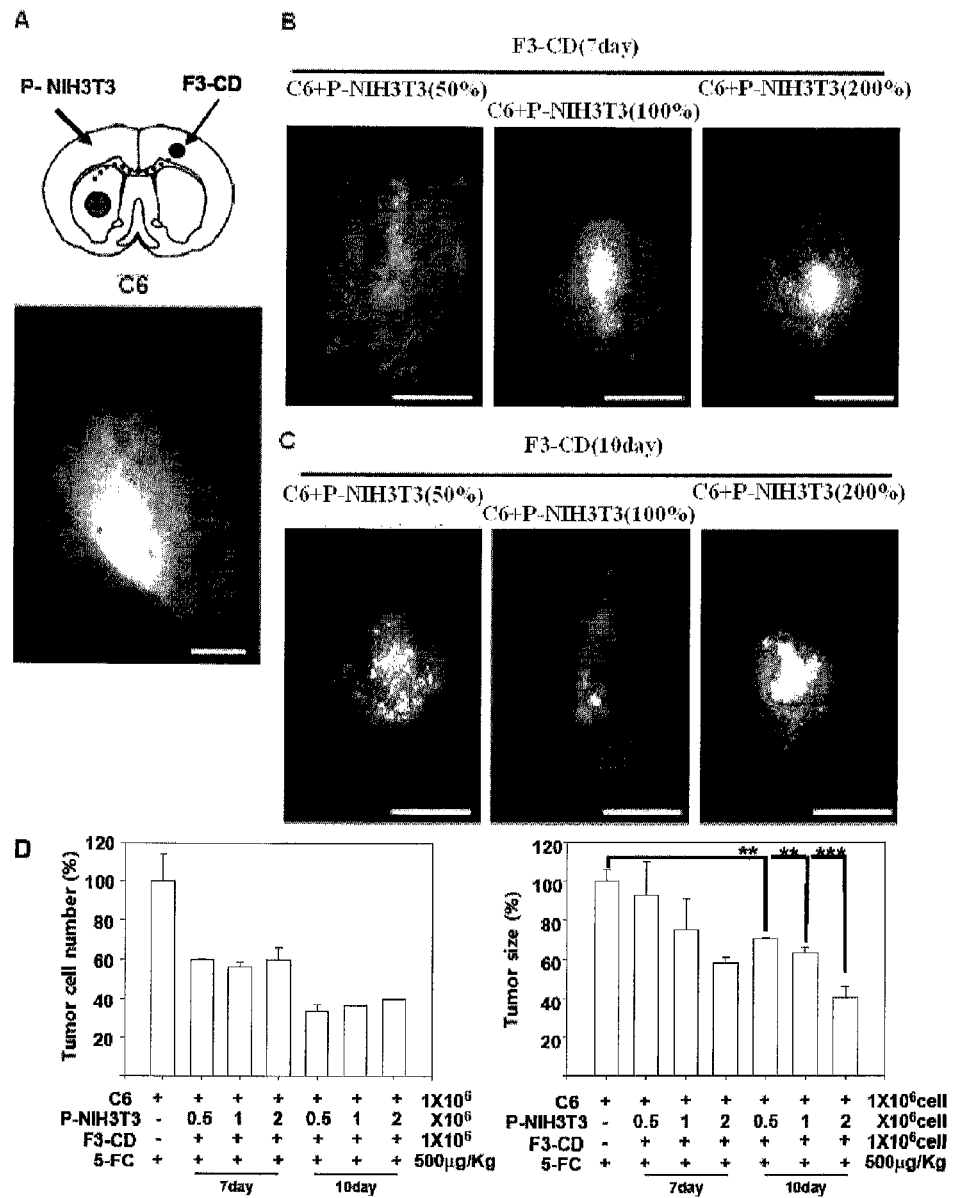
FIG. 14 is a set of photographs and graphs showing that suicide gene-expressing neural stem cells (F3-CD) implanted into a rat brain in a C6 rat glioma model were induced toward periostin-expressing cells and showed the therapeutic effect of killing glioma cells (C6).

As a result, as can be seen in FIG. 14, the direction of migration of F3-CD cells was regulated by the introduction of p-NIH3T3 cells, and the ability to induce the migration of F3-CD cells increased in a manner dependent on the number of p-NIH3T3 cells, so that the F3-CD cells migrated toward the C6 glioma cells. Also, the tumor size of the animal implanted with F3-CD cells decreased to 40% of that of the animal implanted with C6 cells alone, indicating that the growth of brain tumor was significantly inhibited. In addition, the tumor size decreased in proportion to the number of p-NIH3T3 cells inducing F3-CD cells to the tumor mass.

Meanwhile, in the case of the animal implanted with the same number of p-NIH3T3 cells, the tumor size decreased more significantly with time (60%; FIG. 14B). It is believed that the decrease in the tumor size resulted from the inhibition of invasion of C6 glioma cells. In the case of the group implanted with C6 cells alone, it was observed that the invasion of C6 cells occurred so that the C6 cells propagated far from the original area of implantation. However, in the case implanted with the p-NIH3T3 cells, the C6 cells did not propagate far away from the original site of implantation.

Figure 15:
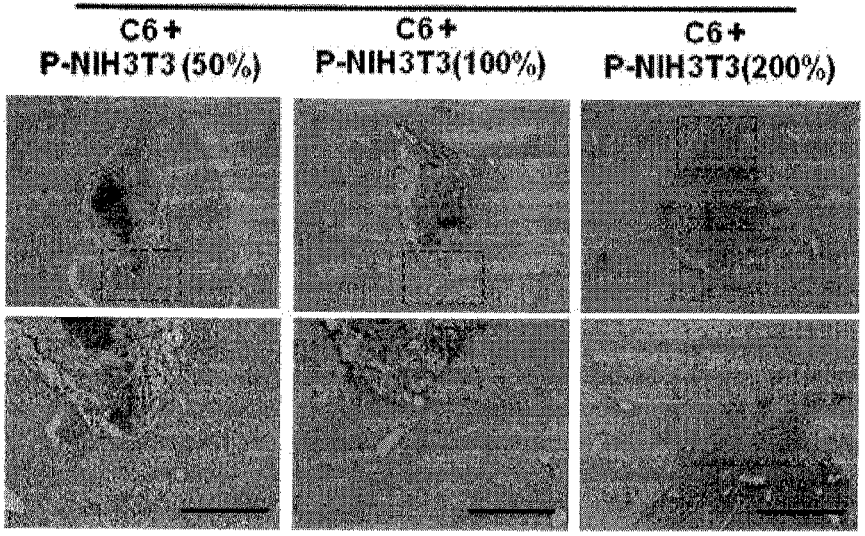
FIG. 15 is a set of close-up photographs showing that the invasion of cancer cells was inhibited when a C6 rat glioma model introduced with periostin-expressing cells was treated with 5-FC. Specifically.
Figure 15:
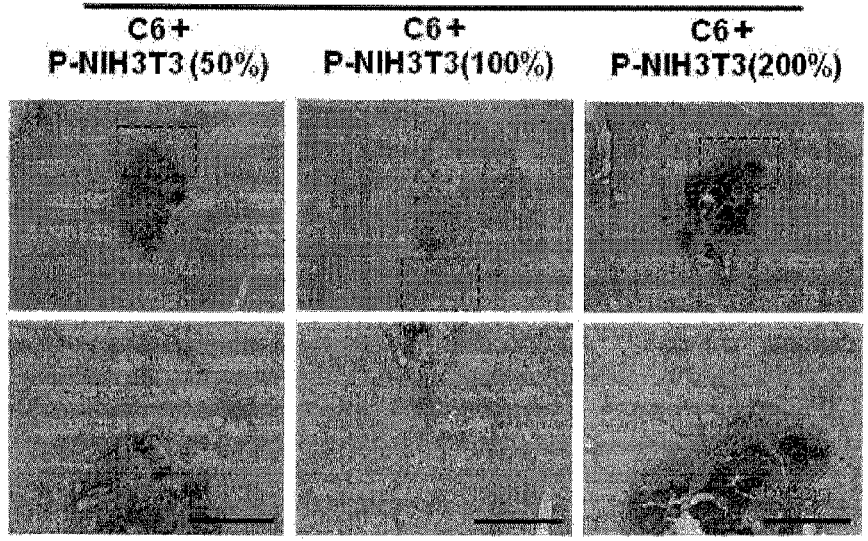

Also, as shown in FIG. 15, the results of H&E staining support that the invasion of rat C6 glioma cells in the animal implanted with the p-NIH3T3 cells was inhibited. FIG. 15 shows the slice of rat brain treated with 5-FC treatment for 2 weeks at 7 (FIG. 15A) or 10 (FIG. 15B) days after F3.CD cells were transplanted.

As described above, the inhibition of invasion of glioma cells is enhanced by the increase in the number of p-NIH3T3 cells and the period of migration of F3-CD cells. Such results indicate that, as the amount of periostin secreted from p-NIH3T3 cells increases, cancer cell targeting of suicide gene-expressing F3 cells can be enhanced, thereby significantly inhibiting the growth of cancer cells. Also, such results suggest that, as the amount of periotin increases, the invasion of cancer cells into normal tissue, which is an important factor in the recurrence of brain cancer, can be effectively inhibited, thereby maximizing the effect of treating tumors.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Sequence Listing

The electronic file was attached.

What is claimed is:

1. A method of treating a glioma the method comprising:
   (a) administering to the area around the glioma a periostin-overexpressing and over-secreting cell transfected by the periostin gene, wherein the transfected cell is a fibroblast or HEK cell;
   (b) administering to the area around the glioma a human neural stem cells transfected with a cytosine deaminase gene, wherein the neural stem cells express cytosine deaminase;
   (c) administering to the area around the glioma 5-fluorocytosine, wherein the cytosine deaminase converts the 5-fluorcytosine to 5-fluoruracil; wherein the oversecreted periostin enhances targeting of the human neural stem cells, and wherein the 5-fluorouracil is in an amount that will kill glioma cells.

2. The method of claim 1, wherein the periostin comprises an amino acid sequence set forth in any one of SEQ ID NO: 1 to SEQ ID NO: 4.

* * * * *

SEQUENCE LISTING

<160> NUMBER OF SEQ ID NOS: 24

<210> SEQ ID NO 1
<211> LENGTH: 776
<212> TYPE: PRT
<213> ORGANISM: Homo sapiens

<400> SEQUENCE: 1

```
Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
            35                  40                  45

Ile Leu Gly Thr Lys Lys Lys Tyr Phe Ser Thr Cys Lys Leu Arg Glu
        50                  55                  60

Glu Ile Glu Gly Lys Gly Ser Phe Thr Tyr Phe Ala Pro Ser Asn Glu
65                  70                  75                  80

Ala Trp Asp Asn Leu Asp Ser Asp Ile Arg Arg Gly Leu Glu Ser Asn
                85                  90                  95

Val Asn Val Glu Leu Leu Asn Ala Leu His Ser His Met Ile Asn Lys
            100                 105                 110

Arg Met Leu Thr Lys Asp Leu Lys Asn Gly Met Ile Ile Pro Ser Met
        115                 120                 125

Tyr Asn Asn Leu Gly Leu Phe Ile Asn His Tyr Pro Asn Gly Val Val
    130                 135                 140

Thr Val Asn Cys Ala Arg Ile Ile His Gly Asn Gln Ile Ala Thr Asn
145                 150                 155                 160

Gly Val Val His Val Ile Asp Arg Val Leu Thr Gln Ile Gly Thr Ser
                165                 170                 175

Ile Gln Asp Phe Ile Glu Ala Glu Asp Asp Leu Ser Ser Phe Arg Ala
            180                 185                 190

Ala Ala Ile Thr Ser Asp Ile Leu Glu Ala Leu Gly Arg Asp Gly His
        195                 200                 205

Phe Thr Leu Phe Ala Pro Thr Asn Glu Ala Phe Glu Lys Leu Pro Arg
    210                 215                 220

Gly Val Leu Glu Arg Ile Met Gly Asp Lys Val Ala Ser Glu Ala Leu
225                 230                 235                 240

Met Lys Tyr His Ile Leu Asn Thr Leu Gln Cys Ser Glu Ser Ile Met
                245                 250                 255

Gly Gly Ala Val Phe Glu Thr Leu Glu Gly Asn Thr Ile Glu Ile Gly
            260                 265                 270

Cys Asp Gly Asp Ser Ile Thr Val Asn Gly Ile Lys Met Val Asn Lys
        275                 280                 285
```

-continued

```
Lys Asp Ile Val Thr Asn Asn Gly Val Ile His Leu Ile Asp Gln Val
290                 295                 300
Leu Ile Pro Asp Ser Ala Lys Gln Val Ile Glu Leu Ala Gly Lys Gln
305                 310                 315                 320
Gln Thr Thr Phe Thr Asp Leu Val Ala Gln Leu Gly Leu Ala Ser Ala
                325                 330                 335
Leu Arg Pro Asp Gly Glu Tyr Thr Leu Leu Ala Pro Val Asn Asn Ala
                340                 345                 350
Phe Ser Asp Asp Thr Leu Ser Met Asp Gln Arg Leu Leu Lys Leu Ile
            355                 360                 365
Leu Gln Asn His Ile Leu Lys Val Lys Val Gly Leu Asn Glu Leu Tyr
370                 375                 380
Asn Gly Gln Ile Leu Glu Thr Ile Gly Gly Lys Gln Leu Arg Val Phe
385                 390                 395                 400
Val Tyr Arg Thr Ala Val Cys Ile Glu Asn Ser Cys Met Glu Lys Gly
                405                 410                 415
Ser Lys Gln Gly Arg Asn Gly Ala Ile His Ile Phe Arg Glu Ile Ile
                420                 425                 430
Lys Pro Ala Glu Lys Ser Leu His Glu Lys Leu Lys Gln Asp Lys Arg
            435                 440                 445
Phe Ser Thr Phe Leu Ser Leu Leu Glu Ala Ala Asp Leu Lys Glu Leu
450                 455                 460
Leu Thr Gln Pro Gly Asp Trp Thr Leu Phe Val Pro Thr Asn Asp Ala
465                 470                 475                 480
Phe Lys Gly Met Thr Ser Glu Glu Lys Glu Ile Leu Ile Arg Asp Lys
                485                 490                 495
Asn Ala Leu Gln Asn Ile Ile Leu Tyr His Leu Thr Pro Gly Val Phe
            500                 505                 510
Ile Gly Lys Gly Phe Glu Pro Gly Val Thr Asn Ile Leu Lys Thr Thr
            515                 520                 525
Gln Gly Ser Lys Ile Phe Leu Lys Glu Val Asn Asp Thr Leu Leu Val
            530                 535                 540
Asn Glu Leu Lys Ser Lys Glu Ser Asp Ile Met Thr Thr Asn Gly Val
545                 550                 555                 560
Ile His Val Val Asp Lys Leu Leu Tyr Pro Ala Asp Thr Pro Val Gly
                565                 570                 575
Asn Asp Gln Leu Leu Glu Ile Leu Asn Lys Leu Ile Lys Tyr Ile Gln
            580                 585                 590
Ile Lys Phe Val Arg Gly Ser Thr Phe Lys Glu Ile Pro Val Thr Val
            595                 600                 605
Tyr Thr Thr Lys Ile Ile Thr Lys Val Val Glu Pro Lys Ile Lys Val
610                 615                 620
Ile Glu Gly Ser Leu Gln Pro Ile Ile Lys Thr Glu Gly Pro Thr Leu
625                 630                 635                 640
Thr Lys Val Lys Ile Glu Gly Glu Pro Glu Phe Arg Leu Ile Lys Glu
                645                 650                 655
Gly Glu Thr Ile Thr Glu Val Ile His Gly Glu Pro Ile Ile Lys Lys
                660                 665                 670
Tyr Thr Lys Ile Ile Asp Gly Val Pro Val Glu Ile Thr Glu Lys Glu
            675                 680                 685
Thr Arg Glu Glu Arg Ile Ile Thr Gly Pro Glu Ile Lys Tyr Thr Arg
690                 695                 700
```

```
Ile Ser Thr Gly Gly Gly Glu Thr Glu Thr Leu Lys Lys Leu Leu
705                 710                 715                 720

Gln Glu Glu Val Thr Lys Val Thr Lys Phe Ile Glu Gly Gly Asp Gly
                725                 730                 735

His Leu Phe Glu Asp Glu Glu Ile Lys Arg Leu Leu Gln Gly Asp Thr
                740                 745                 750

Pro Val Arg Lys Leu Gln Ala Asn Lys Lys Val Gln Gly Ser Arg Arg
                755                 760                 765

Arg Leu Arg Glu Gly Arg Ser Gln
    770                 775

<210> SEQ ID NO 2
<211> LENGTH: 779
<212> TYPE: PRT
<213> ORGANISM: Homo sapiens

<400> SEQUENCE: 2

Met Ile Pro Phe Leu Pro Met Phe Ser Leu Leu Leu Leu Ile Val
1               5                   10                  15

Asn Pro Ile Asn Ala Asn Asn His Tyr Asp Lys Ile Leu Ala His Ser
                20                  25                  30

Arg Ile Arg Gly Arg Asp Gln Gly Pro Asn Val Cys Ala Leu Gln Gln
                35                  40                  45

Ile Leu Gly Thr Lys Lys Lys Tyr Phe Ser Thr Cys Lys Asn Trp Tyr
50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
                100                 105                 110

Thr Gln Arg Tyr Ser Asp Ala Ser Lys Leu Arg Glu Glu Ile Glu Gly
                115                 120                 125

Lys Gly Ser Phe Thr Tyr Phe Ala Pro Ser Asn Glu Ala Trp Asp Asn
                130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
                180                 185                 190

Gly Leu Phe Ile Asn His Tyr Pro Asn Gly Val Val Thr Val Asn Cys
                195                 200                 205

Ala Arg Ile Ile His Gly Asn Gln Ile Ala Thr Asn Gly Val Val His
                210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
                260                 265                 270

Ala Pro Thr Asn Glu Ala Phe Glu Lys Leu Pro Arg Gly Val Leu Glu
                275                 280                 285

Arg Ile Met Gly Asp Lys Val Ala Ser Glu Ala Leu Met Lys Tyr His
                290                 295                 300
```

```
Ile Leu Asn Thr Leu Gln Cys Ser Glu Ser Ile Met Gly Gly Ala Val
305                 310                 315                 320

Phe Glu Thr Leu Glu Gly Asn Thr Ile Glu Ile Gly Cys Asp Gly Asp
            325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
            405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
            565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
            595                 600                 605

Ser Lys Glu Ser Asp Ile Met Thr Thr Asn Gly Val Ile His Val Val
            610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Lys Pro Ile
            660                 665                 670

Ile Lys Lys Tyr Thr Lys Ile Ile Asp Gly Val Pro Val Glu Ile Thr
            675                 680                 685

Glu Lys Glu Thr Arg Glu Glu Arg Ile Ile Thr Gly Pro Glu Ile Lys
            690                 695                 700

Tyr Thr Arg Ile Ser Thr Gly Gly Gly Glu Thr Glu Glu Thr Leu Lys
705                 710                 715                 720
```

-continued

Lys Leu Leu Gln Glu Glu Val Thr Lys Val Thr Lys Phe Ile Glu Gly
                    725                 730                 735

Gly Asp Gly His Leu Phe Glu Asp Glu Glu Ile Lys Arg Leu Leu Gln
            740                 745                 750

Gly Asp Thr Pro Val Arg Lys Leu Gln Ala Asn Lys Lys Val Gln Gly
            755                 760                 765

Ser Arg Arg Arg Leu Arg Glu Gly Arg Ser Gln
770                 775

<210> SEQ ID NO 3
<211> LENGTH: 781
<212> TYPE: PRT
<213> ORGANISM: Homo sapiens

<400> SEQUENCE: 3

Met Ile Pro Phe Leu Pro Met Phe Ser Leu Leu Leu Leu Leu Ile Val
1               5                   10                  15

Asn Pro Ile Asn Ala Asn Asn His Tyr Asp Lys Ile Leu Ala His Ser
            20                  25                  30

Arg Ile Arg Gly Arg Asp Gln Gly Pro Asn Val Cys Ala Leu Gln Gln
        35                  40                  45

Ile Leu Gly Thr Lys Lys Lys Tyr Phe Ser Thr Cys Lys Asn Trp Tyr
    50                  55                  60

Lys Lys Ser Ile Cys Gly Gln Lys Thr Thr Val Leu Tyr Glu Cys Cys
65                  70                  75                  80

Pro Gly Tyr Met Arg Met Glu Gly Met Lys Gly Cys Pro Ala Val Leu
                85                  90                  95

Pro Ile Asp His Val Tyr Gly Thr Leu Gly Ile Val Gly Ala Thr Thr
            100                 105                 110

Thr Gln Arg Tyr Ser Asp Ala Ser Lys Leu Arg Glu Glu Ile Glu Gly
        115                 120                 125

Lys Gly Ser Phe Thr Tyr Phe Ala Pro Ser Asn Glu Ala Trp Asp Asn
    130                 135                 140

Leu Asp Ser Asp Ile Arg Arg Gly Leu Glu Ser Asn Val Asn Val Glu
145                 150                 155                 160

Leu Leu Asn Ala Leu His Ser His Met Ile Asn Lys Arg Met Leu Thr
                165                 170                 175

Lys Asp Leu Lys Asn Gly Met Ile Ile Pro Ser Met Tyr Asn Asn Leu
            180                 185                 190

Gly Leu Phe Ile Asn His Tyr Pro Asn Gly Val Val Thr Val Asn Cys
        195                 200                 205

Ala Arg Ile Ile His Gly Asn Gln Ile Ala Thr Asn Gly Val Val His
    210                 215                 220

Val Ile Asp Arg Val Leu Thr Gln Ile Gly Thr Ser Ile Gln Asp Phe
225                 230                 235                 240

Ile Glu Ala Glu Asp Asp Leu Ser Ser Phe Arg Ala Ala Ala Ile Thr
                245                 250                 255

Ser Asp Ile Leu Glu Ala Leu Gly Arg Asp Gly His Phe Thr Leu Phe
            260                 265                 270

Ala Pro Thr Asn Glu Ala Phe Glu Lys Leu Pro Arg Gly Val Leu Glu
        275                 280                 285

Arg Ile Met Gly Asp Lys Val Ala Ser Glu Ala Leu Met Lys Tyr His
    290                 295                 300

Ile Leu Asn Thr Leu Gln Cys Ser Glu Ser Ile Met Gly Gly Ala Val
305                 310                 315                 320

```
Phe Glu Thr Leu Glu Gly Asn Thr Ile Glu Ile Gly Cys Asp Gly Asp
            325                 330                 335

Ser Ile Thr Val Asn Gly Ile Lys Met Val Asn Lys Lys Asp Ile Val
            340                 345                 350

Thr Asn Asn Gly Val Ile His Leu Ile Asp Gln Val Leu Ile Pro Asp
            355                 360                 365

Ser Ala Lys Gln Val Ile Glu Leu Ala Gly Lys Gln Gln Thr Thr Phe
    370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
            405                 410                 415

Thr Leu Ser Met Asp Gln Arg Leu Leu Lys Leu Ile Leu Gln Asn His
            420                 425                 430

Ile Leu Lys Val Lys Val Gly Leu Asn Glu Leu Tyr Asn Gly Gln Ile
            435                 440                 445

Leu Glu Thr Ile Gly Gly Lys Gln Leu Arg Val Phe Val Tyr Arg Thr
    450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
            485                 490                 495

Lys Ser Leu His Glu Lys Leu Lys Gln Asp Lys Arg Phe Ser Thr Phe
            500                 505                 510

Leu Ser Leu Leu Glu Ala Ala Asp Leu Lys Glu Leu Leu Thr Gln Pro
            515                 520                 525

Gly Asp Trp Thr Leu Phe Val Pro Thr Asn Asp Ala Phe Lys Gly Met
    530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
            565                 570                 575

Phe Glu Pro Gly Val Thr Asn Ile Leu Lys Thr Thr Gln Gly Ser Lys
            580                 585                 590

Ile Phe Leu Lys Glu Val Asn Asp Thr Leu Leu Val Asn Glu Leu Lys
    595                 600                 605

Ser Lys Glu Ser Asp Ile Met Thr Thr Asn Gly Val Ile His Val Val
    610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
            645                 650                 655

Arg Gly Ser Thr Phe Lys Glu Ile Pro Val Thr Val Tyr Arg Pro Thr
            660                 665                 670

Leu Thr Lys Val Lys Ile Glu Gly Glu Pro Glu Phe Arg Leu Ile Lys
            675                 680                 685

Glu Gly Glu Thr Ile Thr Glu Val Ile His Gly Glu Pro Ile Ile Lys
    690                 695                 700

Lys Tyr Thr Lys Ile Ile Asp Gly Val Pro Val Glu Ile Thr Glu Lys
705                 710                 715                 720

Glu Thr Arg Glu Glu Arg Ile Ile Thr Gly Pro Glu Ile Lys Tyr Thr
            725                 730                 735
```

```
Arg Ile Ser Thr Gly Gly Gly Glu Thr Glu Thr Leu Lys Lys Leu
             740                 745                 750
Leu Gln Glu Asp Thr Pro Val Arg Lys Leu Gln Ala Asn Lys Lys Val
        755                 760                 765
Gln Gly Ser Arg Arg Arg Leu Arg Glu Gly Arg Ser Gln
    770                 775                 780

<210> SEQ ID NO 4
<211> LENGTH: 751
<212> TYPE: PRT
<213> ORGANISM: Homo sapiens

<400> SEQUENCE: 4

Met Ile Pro Phe Leu Pro Met Phe Ser Leu Leu Leu Leu Leu Ile Val
1               5                  10                  15
Asn Pro Ile Asn Ala Asn Asn His Tyr Asp Lys Ile Leu Ala His Ser
            20                  25                  30
Arg Ile Arg Gly Arg Asp Gln Gly Pro Asn Val Cys Ala Leu Gln Gln
        35                  40                  45
Ile Leu Gly Thr Lys Lys Lys Tyr Phe Ser Thr Cys Lys Asn Trp Tyr
    50                  55                  60
Lys Lys Ser Ile Cys Gly Gln Lys Thr Thr Val Leu Tyr Glu Cys Cys
65                  70                  75                  80
Pro Gly Tyr Met Arg Met Glu Gly Met Lys Gly Cys Pro Ala Val Leu
                85                  90                  95
Pro Ile Asp His Val Tyr Gly Thr Leu Gly Ile Val Gly Ala Thr Thr
            100                 105                 110
Thr Gln Arg Tyr Ser Asp Ala Ser Lys Leu Arg Glu Glu Ile Glu Gly
        115                 120                 125
Lys Gly Ser Phe Thr Tyr Phe Ala Pro Ser Asn Glu Ala Trp Asp Asn
    130                 135                 140
Leu Asp Ser Asp Ile Arg Arg Gly Leu Glu Ser Asn Val Asn Val Glu
145                 150                 155                 160
Leu Leu Asn Ala Leu His Ser His Met Ile Asn Lys Arg Met Leu Thr
                165                 170                 175
Lys Asp Leu Lys Asn Gly Met Ile Ile Pro Ser Met Tyr Asn Asn Leu
            180                 185                 190
Gly Leu Phe Ile Asn His Tyr Pro Asn Gly Val Val Thr Val Asn Cys
        195                 200                 205
Ala Arg Ile Ile His Gly Asn Gln Ile Ala Thr Asn Gly Val Val His
    210                 215                 220
Val Ile Asp Arg Val Leu Thr Gln Ile Gly Thr Ser Ile Gln Asp Phe
225                 230                 235                 240
Ile Glu Ala Glu Asp Asp Leu Ser Ser Phe Arg Ala Ala Ala Ile Thr
                245                 250                 255
Ser Asp Ile Leu Glu Ala Leu Gly Arg Asp Gly His Phe Thr Leu Phe
            260                 265                 270
Ala Pro Thr Asn Glu Ala Phe Glu Lys Leu Pro Arg Gly Val Leu Glu
        275                 280                 285
Arg Ile Met Gly Asp Lys Val Ala Ser Glu Ala Leu Met Lys Tyr His
    290                 295                 300
Ile Leu Asn Thr Leu Gln Cys Ser Glu Ser Ile Met Gly Gly Ala Val
305                 310                 315                 320
Phe Glu Thr Leu Glu Gly Asn Thr Ile Glu Ile Gly Cys Asp Gly Asp
                325                 330                 335
```

-continued

Ser Ile Thr Val Asn Gly Ile Lys Met Val Asn Lys Asp Ile Val
                340                 345                 350

Thr Asn Asn Gly Val Ile His Leu Ile Asp Gln Val Leu Ile Pro Asp
                355                 360                 365

Ser Ala Lys Gln Val Ile Glu Leu Ala Gly Lys Gln Gln Thr Thr Phe
370                 375                 380

Thr Asp Leu Val Ala Gln Leu Gly Leu Ala Ser Ala Leu Arg Pro Asp
385                 390                 395                 400

Gly Glu Tyr Thr Leu Leu Ala Pro Val Asn Asn Ala Phe Ser Asp Asp
                405                 410                 415

Thr Leu Ser Met Asp Gln Arg Leu Leu Lys Leu Ile Leu Gln Asn His
                420                 425                 430

Ile Leu Lys Val Lys Val Gly Leu Asn Glu Leu Tyr Asn Gly Gln Ile
                435                 440                 445

Leu Glu Thr Ile Gly Gly Lys Gln Leu Arg Val Phe Val Tyr Arg Thr
                450                 455                 460

Ala Val Cys Ile Glu Asn Ser Cys Met Glu Lys Gly Ser Lys Gln Gly
465                 470                 475                 480

Arg Asn Gly Ala Ile His Ile Phe Arg Glu Ile Ile Lys Pro Ala Glu
                485                 490                 495

Lys Ser Leu His Glu Lys Leu Lys Gln Asp Lys Arg Phe Ser Thr Phe
                500                 505                 510

Leu Ser Leu Leu Glu Ala Ala Asp Leu Lys Glu Leu Leu Thr Gln Pro
                515                 520                 525

Gly Asp Trp Thr Leu Phe Val Pro Thr Asn Asp Ala Phe Lys Gly Met
                530                 535                 540

Thr Ser Glu Glu Lys Glu Ile Leu Ile Arg Asp Lys Asn Ala Leu Gln
545                 550                 555                 560

Asn Ile Ile Leu Tyr His Leu Thr Pro Gly Val Phe Ile Gly Lys Gly
                565                 570                 575

Phe Glu Pro Gly Val Thr Asn Ile Leu Lys Thr Thr Gln Gly Ser Lys
                580                 585                 590

Ile Phe Leu Lys Glu Val Asn Asp Thr Leu Leu Val Asn Glu Leu Lys
                595                 600                 605

Ser Lys Glu Ser Asp Ile Met Thr Thr Asn Gly Val Ile His Val Val
                610                 615                 620

Asp Lys Leu Leu Tyr Pro Ala Asp Thr Pro Val Gly Asn Asp Gln Leu
625                 630                 635                 640

Leu Glu Ile Leu Asn Lys Leu Ile Lys Tyr Ile Gln Ile Lys Phe Val
                645                 650                 655

Arg Gly Ser Thr Phe Lys Glu Ile Pro Val Thr Val Tyr Lys Pro Ile
                660                 665                 670

Ile Lys Lys Tyr Thr Lys Ile Ile Asp Gly Val Pro Val Glu Ile Thr
                675                 680                 685

Glu Lys Glu Thr Arg Glu Glu Arg Ile Ile Thr Gly Pro Glu Ile Lys
                690                 695                 700

Tyr Thr Arg Ile Ser Thr Gly Gly Glu Thr Glu Glu Thr Leu Lys
705                 710                 715                 720

Lys Leu Leu Gln Glu Asp Thr Pro Val Arg Lys Leu Gln Ala Asn Lys
                725                 730                 735

Lys Val Gln Gly Ser Arg Arg Leu Arg Glu Gly Arg Ser Gln
                740                 745                 750

```
<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
actgggagca caaggagaac c                                              21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
ccgcttagtg atgagatggt c                                              21

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
ctgcaagaac ggggtgaatg                                                20

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
cacaatgtct accaagccc                                                 19

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
caagctggct gaaaacaaca                                                20

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
actgctcctg gatgcactct                                                20

<210> SEQ ID NO 11
<211> LENGTH: 20
<212> TYPE: DNA
<213> ORGANISM: Artificial
<220> FEATURE:
<223> OTHER INFORMATION: primer
```

```
<400> SEQUENCE: 11
agatgcgaaa gctcaccagt                                              20

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ccgtcattag gctggacaat                                              20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
gccttcactt tgagcactcc                                              20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
ctgctgtact cgctttgcag                                              20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
agcagcttcc atgtcctgag                                              20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gaagttgctg gtgagcttcc                                              20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17
gactccggaa acattctcca                                              20
```

```
<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
ctgacagtcg cagttgcatt                                              20

<210> SEQ ID NO 19
<211> LENGTH: 24
<212> TYPE: DNA
<213> ORGANISM: Artificial
<220> FEATURE:
<223> OTHER INFORMATION: primer

<400> SEQUENCE: 19
agcaatggcc tctacagtcg cagc                                         24

<210> SEQ ID NO 20
<211> LENGTH: 24
<212> TYPE: DNA
<213> ORGANISM: Artificial
<220> FEATURE:
<223> OTHER INFORMATION: primer

<400> SEQUENCE: 20
gcttggagag aaacccagaa agtc                                         24

<210> SEQ ID NO 21
<211> LENGTH: 24
<212> TYPE: DNA
<213> ORGANISM: Artificial
<220> FEATURE:
<223> OTHER INFORMATION: primer

<400> SEQUENCE: 21
ttcatcattt tcatagttac attc                                         24

<210> SEQ ID NO 22
<211> LENGTH: 24
<212> TYPE: DNA
<213> ORGANISM: Artificial
<220> FEATURE:
<223> OTHER INFORMATION: primer

<400> SEQUENCE: 22
cattaagtgt ttaaaaatct tttt                                         24

<210> SEQ ID NO 23
<211> LENGTH: 25
<212> TYPE: DNA
<213> ORGANISM: Artificial
<220> FEATURE:
<223> OTHER INFORMATION: primer

<400> SEQUENCE: 23
gagtcaccgc cagccacacc acggc                                        25

<210> SEQ ID NO 24
<211> LENGTH: 26
<212> TYPE: DNA
```

```
<213> ORGANISM: Artificial
<220> FEATURE:
<223> OTHER INFORMATION: primer

<400> SEQUENCE: 24
gtttgtaatc gatggcttct ggctgc                                          26
```